(12) United States Patent
Micallef

(10) Patent No.: US 9,222,937 B2
(45) Date of Patent: Dec. 29, 2015

(54) METHOD FOR DETECTING NUCLEOSOMES

(75) Inventor: Jacob Vincent Micallef, London (GB)

(73) Assignee: Singapore Volition Pte. Limited, Singapore (SG)

( * ) Notice: Subject to any disclaimer, the term of this patent is extended or adjusted under 35 U.S.C. 154(b) by 0 days.

(21) Appl. No.: 14/239,782

(22) PCT Filed: Aug. 31, 2012

(86) PCT No.: PCT/GB2012/052130
§ 371 (c)(1),
(2), (4) Date: Mar. 27, 2014

(87) PCT Pub. No.: WO2013/030578
PCT Pub. Date: Mar. 7, 2013

(65) Prior Publication Data
US 2014/0206015 A1    Jul. 24, 2014

Related U.S. Application Data

(60) Provisional application No. 61/530,300, filed on Sep. 1, 2011.

(30) Foreign Application Priority Data

Sep. 1, 2011 (GB) .................................. 1115099.2

(51) Int. Cl.
*G01N 33/53* (2006.01)
*G01N 33/68* (2006.01)
(52) U.S. Cl.
CPC ........ *G01N 33/5308* (2013.01); *G01N 33/6875* (2013.01)

(58) Field of Classification Search
None
See application file for complete search history.

(56) References Cited

U.S. PATENT DOCUMENTS 5,011,771 A * 4/1991 Bellet et al. .................. 435/7.94

FOREIGN PATENT DOCUMENTS

WO    WO-99/47924    9/1999
WO    WO-2005/019826    3/2005

OTHER PUBLICATIONS

Active Motif, The Newsletter of, Mar. 2011, 12(1):1-12.
Holdenrieder et al., "Clinical Relevance of Circulating Nucleosomes in Cancer", Annals of the New York Academy of Sciences, 2008, 1137(1):180-189.
Monesteir et al., "Specificities and genetic characteristics of nucleosome-reactive antibodies from autoimmune mice", Mol Immunol, 1996, 33(1):88-99.
PathScan Pan-Methyl-Histone H3 (Lys9) Sandwich ELISA Kit, Cell Signaling Technology, 2012, 1-3.
Salgame et al., "An ELISA for detection of apoptosis", Nucleic Acids Research, 1997, 25(3):680-681.
Van Bavel et al., "Lupus-derived monoclonal autoantibodies against apoptotic chromatin recognize acetylated conformational epitopes", Mol Immunol, 2010, 48:248-256.

* cited by examiner

*Primary Examiner* — Jacob Cheu
(74) *Attorney, Agent, or Firm* — Foley & Lardner LLP

(57) ABSTRACT

The invention relates to a method for detecting and measuring the presence of mono-nucleosomes and oligo-nucleosomes and the use of such measurements for the detection and diagnosis of disease.

17 Claims, 12 Drawing Sheets

METHOD FOR DETECTING NUCLEOSOMES

CROSS-REFERENCE TO RELATED APPLICATIONS

This application is the U.S. national stage application of International Patent Application No. PCT/GB2012/052130, filed on Aug. 31, 2012, which claims priority to GB Application No. 1115099.2, filed on Sep. 1, 2011, and U.S. Provisional Application No. 61/530,300, filed on Sep. 1, 2011. The contents of these applications are incorporated herein by reference in their entirety.

FIELD OF THE INVENTION

The invention relates to a method for detecting and measuring the presence of mono-nucleosomes and oligo-nucleosomes and the use of such measurements for the detection and diagnosis of disease.

BACKGROUND OF THE INVENTION

The human body comprises several hundred cell types. All of these cell types contain the same genome but have widely different phenotypes and different functions in the body. This phenotypic diversity is due to the differential expression of the genome in different cell types. The control of differential gene expression is not entirely understood but the basic mechanisms include gene regulation by a number of interconnected epigenetic signals associated with the gene, including control of the chromatin packing as euchromatin or heterochromatin, control of nucleosome positioning and nuclease accessible sites, methylation of DNA and variation in the structure of the nucleosomes around which the DNA is wrapped.

The nucleosome is the basic unit of chromatin structure and consists of a protein complex of eight highly conserved core histones (comprising a pair of each of the histones H2A, H2B, H3, and H4). Around this complex is wrapped approximately 146 base pairs of DNA. Another histone, H1 or H5, acts as a linker and is involved in chromatin compaction. The DNA is wound around consecutive nucleosomes in a structure often said to resemble "beads on a string" and this forms the basic structure of open or euchromatin. In compacted or heterochromatin this string is coiled and super coiled into a closed and complex structure (Herranz and Esteller, 2007).

The structure of nucleosomes can vary by Post Transcriptional Modification (PTM) of histone proteins and by the inclusion of variant histone proteins. PTM of histone proteins typically occurs on the tails of the core histones and common modifications include acetylation, methylation or ubiquitination of lysine residues as well as methylation of arginine residues and phosphorylation of serine residues. Histone modifications are known to be involved in epigenetic regulation of gene expression (Herranz and Esteller, 2007). The structure of the nucleosome can also vary by the inclusion of alternative histone isoforms or variants which are different gene or splice products and have different amino acid sequences. Histone variants can be classed into a number of families which are subdivided into individual types. The nucleotide sequences of a large number of histone variants are known and publicly available for example in the National Human Genome Research Institute NHGRI Histone Data-Base (Marino-Ramirez, L., Levine, K. M., Morales, M., Zhang, S., Moreland, R. T., Baxevanis, A. D., and Landsman, D. The Histone Database: an integrated resource for histones and histone fold-containing proteins. Database Vol. 2011. (Submitted) and http://genome.nhgri.nih.gov/histones/complete.shtml), the GenBank (NIH genetic sequence) DataBase, the EMBL Nucleotide Sequence Database and the DNA Data Bank of Japan (DDBJ).

Normal cell turnover in adult humans involves the creation by cell division of some $10^{11}$ cells daily and the death of a similar number, mainly by apoptosis. During the process of apoptosis chromatin is broken down into mononucleosomes and oligonucleosomes which are released from the cells. Under normal condition the levels of circulating nucleosomes found in healthy subjects is reported to be low. Elevated levels are found in subjects with a variety of conditions including many cancers, auto-immune diseases, inflammatory conditions, stroke and myocardial infarction (Holdenreider & Stieber, 2009).

Mononucleosomes and oligonucleosomes can be detected by Enzyme-Linked ImmunoSorbant Assay (ELISA) and several methods have been reported (Salgame et al, 1997; Holdenrieder et al, 2001; van Nieuwenhuijze et al, 2003). These assays typically employ a monoclonal anti-histone antibody (for example anti-H2B, anti-H3 or anti-H1, H2A, H2B, H3 and H4) as capture antibody and a monoclonal anti-DNA or anti-H2A-H2B-DNA complex antibody as detection antibody. Using these assays workers in the field report that the level of nucleosomes in serum is higher (by up to an order of magnitude) than in plasma samples taken from the same patients. This is also true for serum and plasma measurements of DNA made by PCR (Holdenrieder et al, 2005). The reason for this is not known but the authors speculate that it may be due to additional release of DNA during the clotting process. However, we have found that the results of nucleosome ELISA assays of the current art do not agree with each other. Furthermore, although most circulating DNA in serum or plasma is reported to exist as mono-nucleosomes and oligo-nucleosomes (Holdenrieder et al, 2001), measured levels of nucleosomes and DNA in serum or plasma do not agree well. The correlation coefficient between ELISA results for circulating cell free nucleosomes levels and circulating DNA levels as measured by real time PCR (Polymerase Chain Reaction) has been reported to be $r=0.531$ in serum and $r=0.350$ in plasma (Holdenrieder et al, 2005).

Current nucleosome ELISA methods are used in cell culture, primarily as a method to detect apoptosis (Salgame et al, 1997; Holdenrieder et al, 2001; van Nieuwenhuijze et al, 2003), and are also used for the measurement of circulating cell free nucleosomes in serum and plasma (Holdenrieder et al, 2001). Cell free serum and plasma nucleosome levels released into the circulation by dying cells have been measured by ELISA methods in studies of a number of different cancers to evaluate their use as a potential biomarker (Holdenrieder et al, 2001). Mean circulating nucleosome levels are reported to be high in most, but not all, cancers studied. The highest circulating nucleosome levels were observed in lung cancer subjects. The lowest levels were observed in prostate cancer, which were within the normal range of healthy subjects. However, patients with malignant tumours are reported to have serum nucleosome concentrations that varied considerably and some patients with advanced tumour disease were found to have low circulating nucleosome levels, within the range measured for healthy subjects (Holdenrieder et al, 2001). Because of this and the variety of non-cancer causes of raised nucleosome levels, circulating nucleosome levels are not used clinically as a biomarker of cancer (Holdenrieder and Stieber, 2009). Surprisingly we have shown that many cancer subjects whose circulating nucleosome levels are low or undetectable as measured by these nucleosome ELISA methods of the current art, do in fact have raised levels of circulating cell free nucleosomes. We have designed and demonstrated novel ELISA methods for nucleosomes that detect nucleosomes not detected by ELISA methods of the current art.

ELISA methods for the detection of histone PTMs are also known in the art. ELISA methods for PTM detection in free histones (not in nucleosomes) are used for the detection of PTMs in histones extracted, usually by acid extraction, from cell lysates. Immunoassay for the detection of PTMs in circulating nucleosomes has been reported (Bawden et al, 2005). A method for ELISA detection of histone PTMs in purified nucleosomes directly coated to microtitre wells has recently been reported (Dai et al, 2011). In this method nucleosomes obtained by digestion of chromatin extracts from cultured cells are coated directly to microtitre wells and reacted with anti-PTM antibodies. It will be clear to those skilled in the art that this method requires relatively pure nucleosome samples and is not suitable for the direct measurement of histone PTMs in complex biological media such as blood, plasma or serum. We have developed an ELISA method for intact nucleosomes containing a specific histone PTM and used it to assay blood samples taken from healthy and diseased subjects. Surprisingly, we have shown that nucleosomes containing histone PTMs can be detected in blood samples in which nucleosomes are not detected by nucleosome ELISA methods of the current art.

A modified chromatin immunoprecipitation method for the detection of a histone PTM (H3K9Me, histone H3 monomethylated at lysine residue K9) in cell free nucleosomes associated with a particular DNA sequence has been reported in plasma. The level of sequence specific histone methylation was reported to be independent of the concentration of circulating nucleosomes (Deligezer et al, 2008).

Histone variants (also known as histone isoforms) are known to be epigenetic regulators of gene expression (Herranz and Esteller, 2007). Histone variants have been studied in vivo and in vitro using a variety of techniques including knock-down studies of the gene encoding a particular variant (for example using RNAi knock-down), chromatin immunoprecipitation, stable isotope labeling of amino acids and quantitative mass spectrometry proteomics, immunohistochemistry and Western Blotting (Whittle et al, 2008; Boulard et al, 2010; Sporn et al, 2009; Kapoor et al, 2010; Zee et al, 2010; Hua et al, 2008).

Immunohistochemistry studies of histone variant expression in tissue samples removed at surgery or by biopsy from subjects diagnosed with lung cancer, breast cancer and melanoma have been reported. These immunohistochemistry studies report that staining of histone macroH2A (mH2A) and H2AZ variants in resected cancer tissue samples may have prognostic application in these cancers (Sporn et al, 2009, Hua et al, 2008, Kapoor et al, 2010). One disadvantage of immunohistochemical methods for clinical use is that tissue sample collection is invasive involving surgery or biopsy. Another disadvantage of immunohistochemistry methods is that they are unsuited for early diagnosis or for screening diagnostics as a reasonable expectation of the disease must usually already exist before a biopsy or tissue resection is made. Minimally invasive blood ELISA tests are suitable for a wider range of applications and would overcome these disadvantages and be preferable for the patient as well as faster, lower cost and more high-throughput for the healthcare provider.

However, cell free histone variants in nucleosomes have not been measured in blood. No studies on the presence or absence of histone variants in cell free nucleosomes in blood have been reported nor whether they have value as blood biomarkers of disease. There are currently no methods for the detection or measurement of histone variants in intact cell free nucleosomes. We now report methods for such tests and their use in blood samples taken from healthy and diseased subjects. Surprisingly we have shown that intact nucleosomes comprising specific histone variants and post-translational modifications can be detected in samples for which few or no nucleosomes are detected by nucleosome ELISA methods of the current art.

In addition to the epigenetic signaling mediated by nucleosome structure and position, control of gene expression in cells is also mediated by the methylation status of DNA. It has been known in the art for some time that DNA may be methylated at the 5 position of cytosine nucleotides to form 5-methylcytosine. Methylated DNA in the form of 5-methylcytosine is reported to occur at positions in the DNA sequence where a cytosine nucleotide occurs next to a guanine nucleotide. These positions are termed "CpG" for shorthand. It is reported that more than 70% of CpG positions are methylated in vertebrates (Pennings et al, 2005). Regions of the genome that contain a high proportion of CpG sites are often termed "CpG islands", and approximately 60% of human gene promoter sequences are associated with such CpG islands (Rodriguez-Paredes and Esteller, 2011). In active genes these CpG islands are generally hypomethylated. Methylation of gene promoter sequences is associated with stable gene inactivation. DNA methylation also commonly occurs in repetitive elements including Alu repetitive elements and long interspersed nucleotide elements (Herranz and Estellar, 2007; Allen et al, 2004).

The involvement of DNA methylation in cancer was reported as early as 1983 (Feinberg and Vogelstein, 1983). DNA methylation patterns observed in cancer cells differ from those of healthy cells. Repetitive elements, particularly around pericentromeric areas, are reported to be hypomethylated in cancer relative to healthy cells but promoters of specific genes have been reported to be hypermethylated in cancer. The balance of these two effects is reported to result in global DNA hypomethylation in cancer cells (Rodriguez-Paredes; Esteller, 2007).

Hypermethylation of certain specific genes can be used as a diagnostic biomarker for cancers. For example a method reported for detection of hypermethylation of the Septin 9 gene by PCR amplification of DNA extracted from plasma was reported to detect 72% of colon cancers with a false positive rate of 10% (Grutzmann et al, 2008). The DNA methylation status of specific genes or loci is usually detected by selective bisulphite deamination of cytosine, but not 5-methylcytosine, to uracil, leading to a primary DNA sequence change that can be detected by sequencing or other means (Allen et al, 2004).

Global DNA hypomethylation is a hallmark of cancer cells (Estellar 2007 and Hervouet et al, 2010). Global DNA methylation can be studied in cells using immunohistochemistry techniques. Alternatively the DNA is extracted from the cells for analysis. A number of methods have been reported for the detection of global methylation in DNA extracted from cells including restriction digestion and nearest-neighbour analysis, fluorescent assays using chloracetaldehyde, inverse determination by methylation of all CpG sites using DNA methyltransferase in conjunction with tritium-labeled S-adenosyl methionine to calculate the amount of unmethylated CpG and digestion of DNA into single nucleotides for analysis by high-performance liquid chromatography, thin-layer chromatography, or liquid chromatography followed by mass spectroscopy. The disadvantages of these methods are that they are labour intensive and/or require large amounts of good quality extracted DNA (Allen et al 2004). PCR based methods involving bisulfite deamination overcome the need for large amounts of DNA but must amplify specific genome regions, typically repetitive sequences, as indicative of the total genome content of 5-methylcytosine (Allen et al 2004). These methods for global DNA methylation measurement have been used to study DNA extracted from a variety of cells and tissues. Some workers have studied DNA extracted from white blood cells in whole blood as this is easier to obtain in a minimally-invasive manner (Moore et al, 2008; Ting Hsiung et al, 2007; Mansour et al, 2010). Liquid Chromatography with mass spectrometry is considered the gold standard for global DNA methylation measurement but it is costly, and the DNA must be digested to the single nucleotide level prior to analysis (Vasser et al, 2009).

Recent methods for the estimation of global DNA methylation include ultra high-pressure liquid chromatography with mass spectrometry of hydrolysed DNA extracted from tissue (Zhang et al, 2011) and a methylation-specific digital sequencing (MSDS) method (Ogoshi et al 2011). A classical competitive immunoassay for global DNA methylation (as well as a similar assay for global 5-hydroxymethylcytosine methylation) has been described. In this method DNA extracted from cells or tissues is added to a microtitre well coated with a 5-methylated cytidine conjugate, an anti-5-methylcytidine antibody is added and the distribution of antibody binding between the coated 5-methylcytidine conjugate and the methylated DNA in the extracted sample is compared to that of known standards to estimate the global DNA methylation level present in the sample (Cell Biolabs, 2011). In another immunoassay like method DNA extracted from tissues or from plasma or serum samples is coated to a microtitre well and methylated DNA is detected using an anti-5-methylcytosine antibody (Vasser, et al, 2009; Epigentek, 2009). A disadvantage of these methods is that they require extraction of DNA. They are not suited for example; for the direct measurement of global DNA methylation in biological fluids such as tissue lysate, blood, plasma or serum.

5-Hydroxymethyl modification of cytosine bases in DNA has also been reported. The role of 5-hydroxymethylation is not yet well understood but it appears to be involved in gene regulation (Stroud et al, 2011).

Current methods for the detection of global DNA methylation involve extraction or purification of the DNA and are not suitable for rapid, high throughput, low cost, minimally-invasive diagnostic methods. Similarly, analysis of DNA for other modified or unusual bases (for example uracil, inosine, xanthine, hypoxanthine) can only be investigated by the analysis of substantially pure or extracted DNA. Such analysis cannot be carried out directly in complex biological media such as tissue lysate, blood, plasma or serum.

We now report simple immunoassay methods for the direct estimation of nucleosome associated 5-methyl cytosine and 5-hydroxymethyl cytosine DNA methylation in biological samples without extraction. Surprisingly we have shown that nucleosome associated methylated DNA can be detected in samples in which nucleosomes are not detected by ELISA methods of the current art.

In addition we now report a new immunoassay method designed to detect multiple nucleosome epitopes in a single assay such that a wide range of nucleosome structures are detected, in order to detect nucleosomes which are not detected by methods of the current art. The design further involves optimal selection of suitable nucleosome epitopes in order to maximize the detection of nucleosomes present in a sample.

SUMMARY OF THE INVENTION

According to a first aspect of the invention there is provided a method for detecting nucleosomes in a sample which comprises the steps of:
  (i) contacting the sample with two or more binding agents which bind to different or separate nucleosome epitopes;
  (ii) detecting or quantifying the binding of said multiple binding agents to nucleosomes in the sample; and
  (iii) using the presence or degree of such binding as a measure of the presence of nucleosomes in the sample.

According to a second aspect of the invention there is provided a method for detecting nucleosomes in a sample which comprises the steps of:
  (i) contacting the sample with a first binding agent which binds to nucleosomes;
  (ii) contacting the nucleosomes or sample with two or more second binding agents which bind to different or separate nucleosome epitopes;
  (iii) detecting or quantifying the binding of said multiple second binding agents to nucleosomes in the sample; and
  (iv) using the presence or degree of such binding as a measure of the presence of nucleosomes in the sample.

According to a third aspect of the invention there is provided a method for detecting nucleosomes in a sample which comprises the steps of:
  (i) contacting the sample with two or more first binding agents which bind to different or separate nucleosome epitopes;
  (ii) contacting the nucleosomes or sample with a second binding agent which binds to nucleosomes;
  (iii) detecting or quantifying the binding of said second binding agent to nucleosomes in the sample; and
  (iv) using the presence or degree of such binding as a measure of the presence of nucleosomes in the sample.

According to a fourth aspect of the invention there is provided a method for detecting nucleosomes in a sample which comprises the steps of:
  (i) contacting the sample with two or more first binding agents which bind to different or separate nucleosome epitopes;
  (ii) contacting the nucleosomes or sample with two or more second binding agents which bind to different or separate nucleosome epitopes;
  (iii) detecting or quantifying the binding of said second binding agents to nucleosomes in the sample; and
  (iv) using the presence or degree of such binding as a measure of the presence of nucleosomes in the sample.

According to a further aspect of the invention there is provided a method for detecting nucleosomes in a sample which comprises the steps of:
  (i) contacting the sample with one or more anti-nucleosome polyclonal antibodies or purified fractions thereof;
  (ii) contacting the nucleosomes or sample with a second antibody or other binder which binds to nucleosomes;
  (iii) detecting or quantifying the binding of said second antibody or other binder to nucleosomes in the sample; and
  (iv) using the presence or degree of such binding as a measure of the presence of nucleosomes in the sample.

According to a further aspect of the invention there is provided a method for detecting nucleosomes in a sample which comprises the steps of:
  (i) contacting the sample with a first antibody or other binder which binds to nucleosomes;

(ii) contacting the sample with one or more anti-nucleosome polyclonal second antibodies or purified fractions thereof;
(iii) detecting or quantifying the binding of said second antibody or antibodies to nucleosomes in the sample; and
(iv) using the presence or degree of such binding as a measure of the presence of nucleosomes in the sample.

According to a further aspect of the invention there is provided a method for detecting nucleosomes in a sample which comprises the steps of:
(i) contacting the sample with one or more anti-nucleosome polyclonal antibodies or purified fractions thereof;
(ii) contacting the sample with one or more anti-nucleosome polyclonal second antibodies or purified fractions thereof;
(iii) detecting or quantifying the binding of said second antibody or antibodies to nucleosomes in the sample; and
(iv) using the presence or degree of such binding as a measure of the presence of nucleosomes in the sample.

According to a further aspect of the invention there is provided a method for detecting or diagnosing a disease status in animals or humans which comprises the steps of:
(i) detecting or measuring nucleosomes in a body fluid of a subject according to a method of the invention; and
(ii) using the nucleosome level detected to identify the disease status of the subject.

According to a further aspect of the invention there is provided a method for assessment of an animal or a human subject for suitability for a medical treatment which comprises the steps of:
(i) detecting or measuring nucleosomes in a body fluid of a subject according to a method of the invention; and
(ii) using the nucleosome level detected as a parameter for selection of a suitable treatment for the subject.

According to a further aspect of the invention there is provided a method for monitoring a treatment of an animal or a human subject which comprises the steps of:
(i) detecting or measuring nucleosomes in a body fluid of a subject according to a method of the invention;
(ii) repeating the detection or measurement of nucleosomes in a body fluid of a subject on one or more occasions; and
(iii) using any changes in the nucleosome level detected as a parameter for any changes in the condition of the subject.

According to a further aspect of the invention there is provided a kit for the detection of nucleosomes which comprises antibodies, ligands or binders specific for nucleosomes or component part thereof, or a structural/shape mimic of nucleosomes or component part thereof, together with instructions for use of the kit in accordance with a method of the invention.

DETAILED DESCRIPTION OF THE INVENTION

According to a first aspect of the invention there is provided a method for detecting nucleosomes in a sample which comprises the steps of:
(i) contacting the sample with two or more binding agents which bind to different or separate nucleosome epitopes;
(ii) detecting or quantifying the binding of said multiple binding agents to nucleosomes in the sample; and
(iii) using the presence or degree of such binding as a measure of the presence of nucleosomes in the sample.

We have developed ELISA tests for the individual detection and measurement of nucleosomes containing the histone variants macroH2A1.1 (mH2A1.1), macroH2A2 (mH2A2) and H2AZ. We have used an anti-histone antibody as capture antibody for these assays in combination with an appropriate specific anti-histone variant antibody as detection antibody. We have shown that these ELISA methods work with alternative anti-nucleosome capture antibodies.

We have developed ELISA tests for the individual detection and measurement of nucleosomes containing the DNA bases 5-methylcytosine and 5-hydroxymethylcytosine. We have used an anti-histone antibody as capture antibody for these assays in combination with an appropriate specific anti-nucleotide antibody.

We have also developed an ELISA for the individual detection of nucleosomes containing the histone PTM phosphorylated serine 139 on histone H2AX (P-H2AX(Ser139)).

Figure 14:
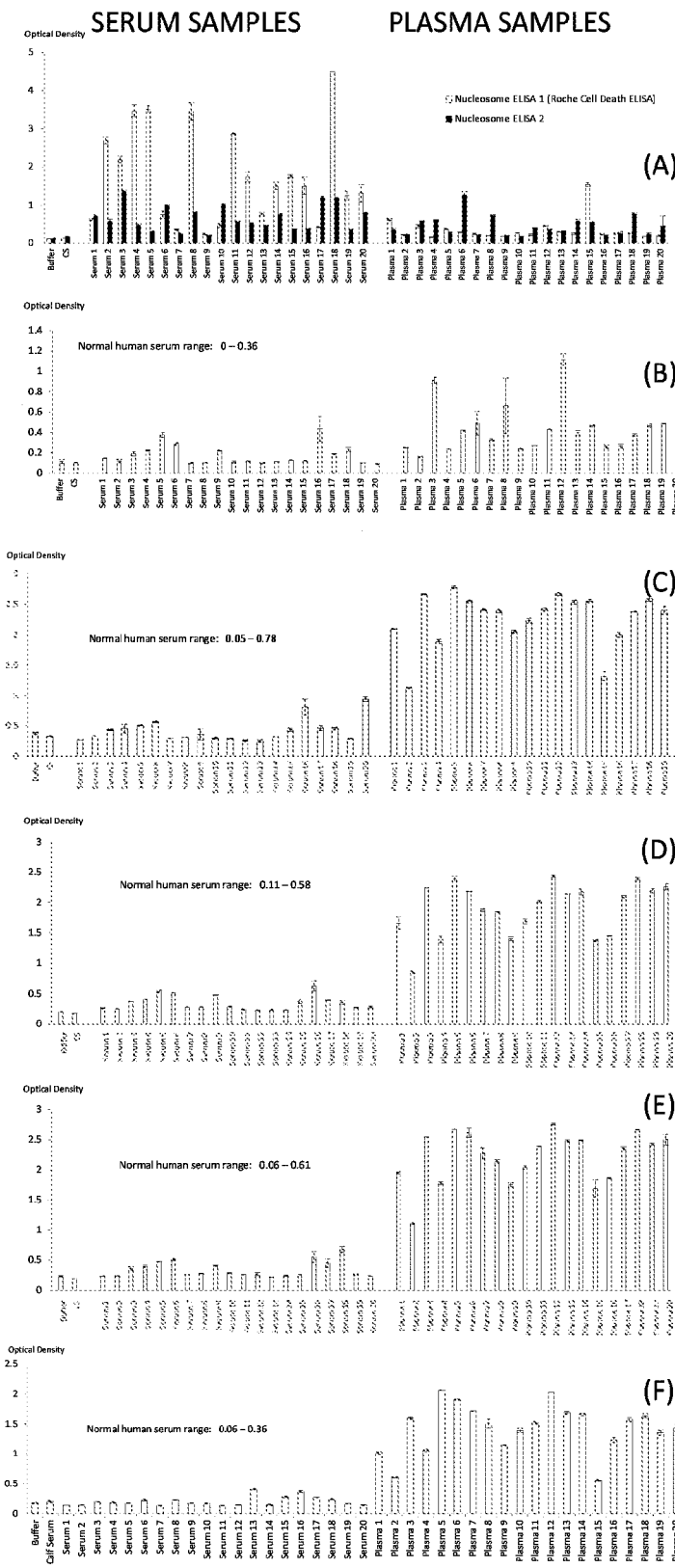
FIG. 14. Cell free nucleosomes detected in 20 serum and 20 EDTA plasma samples taken from healthy volunteers using (A) two ELISA methods of the current art (B) an individual method of the invention for nucleosome associated levels of histone variant mH2A1.1, (C) an individual method of the invention for nucleosome associated levels of histone variant mH2A2, (D) an individual method of the invention for nucleosome associated levels of histone variant H2AZ, (E) an individual method of the invention for nucleosome associated levels of histone modification P-H2AX(Ser139), (F) an individual method of the invention for nucleosome associated levels of 5-methylcytosine methylated DNA.

We used two nucleosome ELISA methods of the current art to measure the circulating cell free nucleosome content of serum and plasma blood samples taken from 20 healthy subjects. The first current ELISA method (ELISA 1) was the Roche Cell Death ELISA and the other (ELISA 2) an ELISA employing a monoclonal anti-histone capture antibody and a monoclonal anti-histone-DNA complex detection antibody. The nucleosome levels detected by both current nucleosome ELISA methods were lower in normal plasma than in normal serum. The results are shown in FIG. 14. This finding is consistent with the published literature (Holdenrieder et al, 2005).

We also measured the individual levels of nucleosomes containing three nucleosome associated histone variants, a histone PTM and a nucleotide in the same samples. The results showed that the serum samples taken from healthy subjects have uniformly low levels of nucleosomes containing histone variants or PTM or nucleotides. Surprisingly, the measured plasma results were higher for all 20 healthy subjects. Thus the results for the method of the invention (plasma higher than serum) are different to those of the methods of the current art (serum higher than plasma) and this result is reproducible for multiple methods of the current art and for multiple (individual) assays of the invention. The results are shown in FIG. 14.

We then used two ELISA methods of the current art to measure the levels of circulating cell free nucleosomes in 19 blood samples taken from 3 patients with colon cancer, 13 patients with lung cancer, 2 patients with pancreatic cancer and 1 patient with oral cancer. Nucleosome levels were low in most of the 19 samples as shown in FIGS. 10-13.

We used ELISA methods for the individual detection of 3 nucleosome associated histone isoforms, 2 nucleosome associated nucleotides and nucleosome associated histone PTM to measure nucleosomes in the same 19 samples. Surprisingly, nucleosomes containing the histone isoforms; macroH2A2 (mH2A2) and H2AZ were detectable in 16 of the 19 samples. Furthermore, nucleosomes containing 5-methylcytosine were detectable in all of the 19 samples taken from cancer subjects. Thus the individual ELISA methods described provide novel nucleosome ELISA methods capable of detecting nucleosomes not detected, or detected in much lower amounts, by nucleosome assays of the current art (FIGS. 10-13).

We have also developed an assay for the individual detection of nucleosomes containing the common nucleotide thymine using an anti-thymine dimer antibody. We tested this assay for the presence of nucleosomes containing thymine in the three cancer samples in which nucleosomes were not detectable by ELISA methods for histone variants or a histone PTM. The results of this assay were that nucleosomes containing thymine were also not detectable in these 3 samples taken from cancer subjects.

Figure 9:
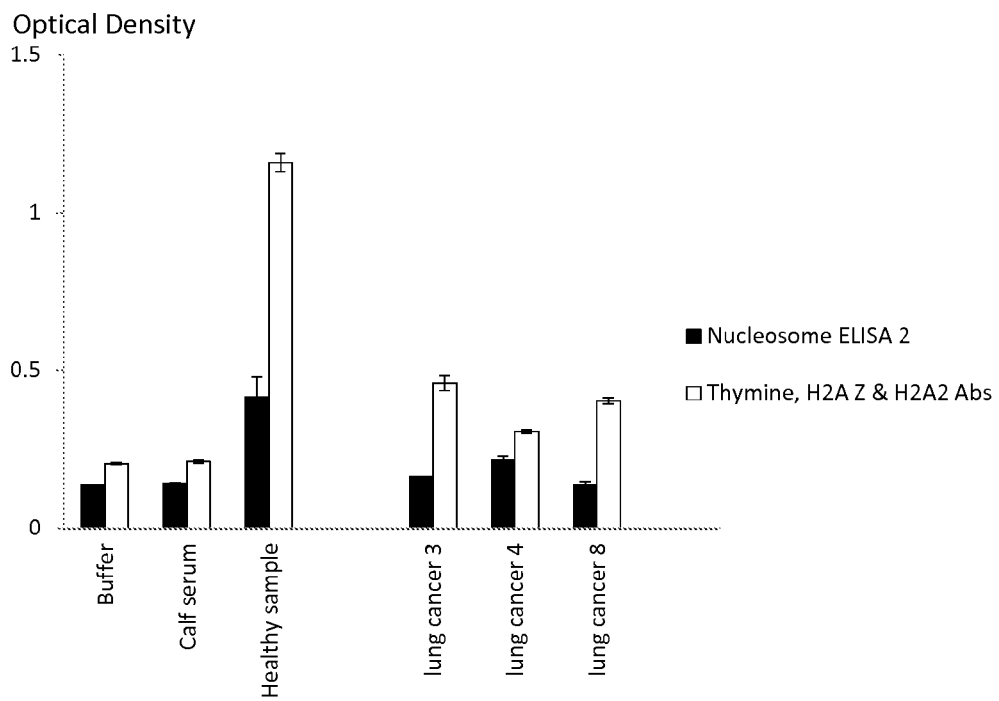
FIG. 9. Detection of nucleosomes using an ELISA method of the invention directed at multiple epitopes in a blood nucleosome sample prepared from healthy subjects and 3 blood samples taken from lung cancer subjects in which nucleosomes were very low or undetectable by the individual assays. Results for a nucleosome ELISA method of the current art (ELISA 2) are shown for comparison.
Figure 10:
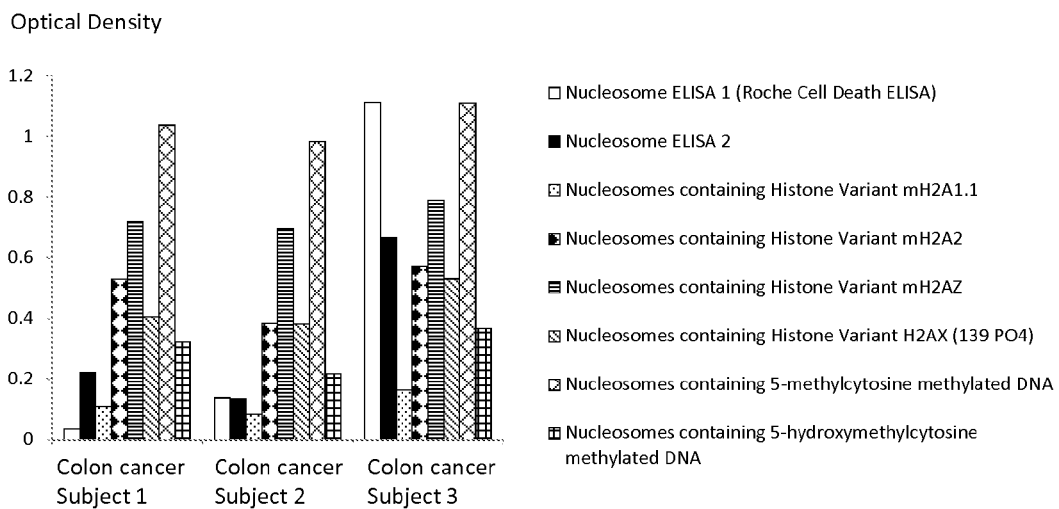
FIG. 10. Cell free nucleosomes detected by individual assay of a variety of histone and nucleotide epitopes in EDTA plasma samples taken from 3 colon cancer subjects.
Figure 11:
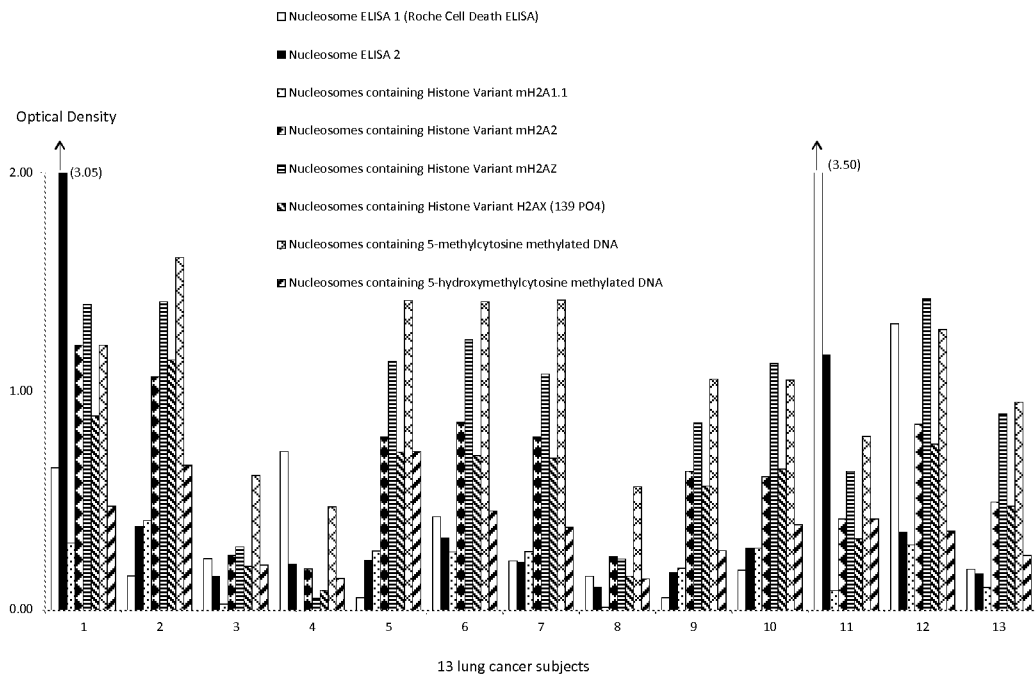
FIG. 11. Cell free nucleosomes detected by individual assay of a variety of histone and nucleotide epitopes in EDTA plasma samples taken from 13 lung cancer subjects.
Figure 12:
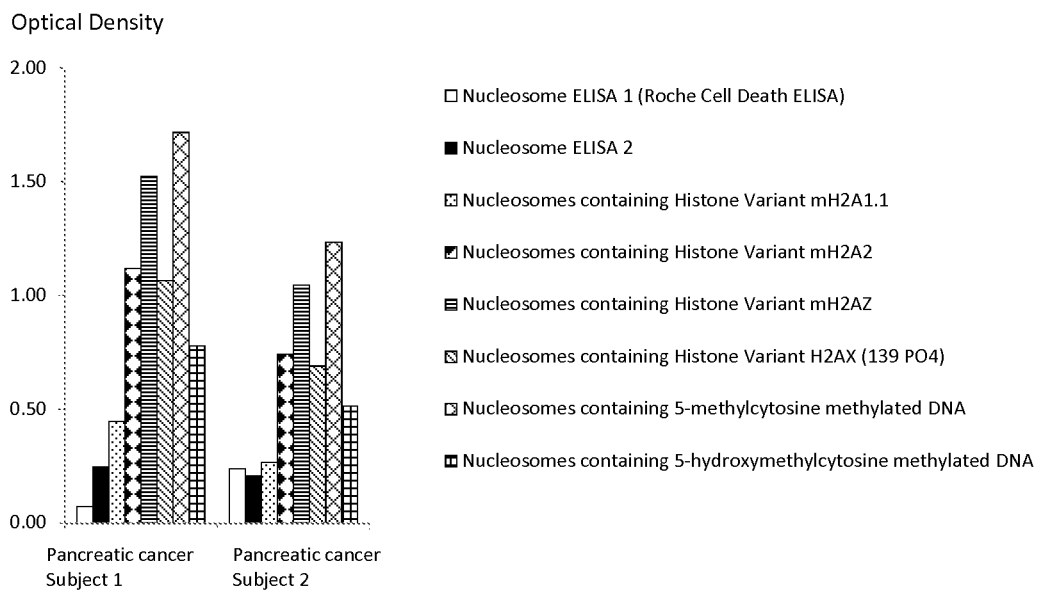
FIG. 12. Cell free nucleosomes detected by individual assay of a variety of histone and nucleotide epitopes in EDTA plasma samples taken from 2 pancreatic cancer subjects.
Figure 13:
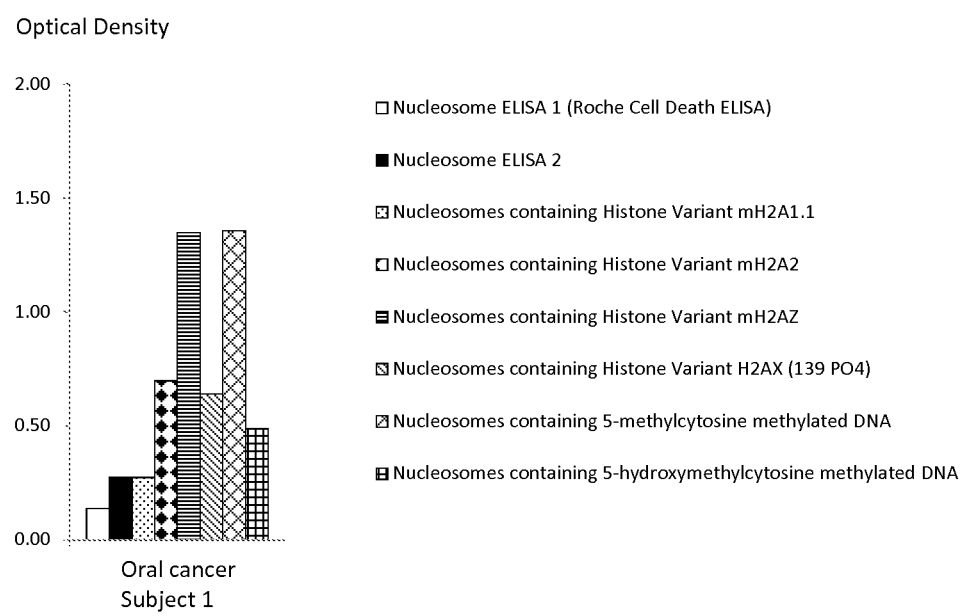
FIG. 13. Cell free nucleosomes detected by individual assay of a variety of histone and nucleotide epitopes in an EDTA plasma samples taken from 1 oral cancer subject.

We selected the 3 samples for which the nucleosome ELISA methods of the current art, the individual nucleosome associated thymine assay as well individual assays for nucleosome associated histone variants and a PTM, all failed to detect the presence of any significant level of nucleosomes. Surprisingly, when the same 3 samples were assayed for the same nucleosome epitopes using the same antibodies as the individual assays for thymine and the histone variants mH2A2 and H2AZ, but using the method of the invention involving simultaneous assay of these multiple epitopes; significant levels of nucleosomes were detected (FIG. 9). Thus the multiple epitope method of the invention detects nucleosomes in samples where none are detectable by methods of the current art or by individual epitope assays.

Multiple isoforms or variants have been reported for histones H2A, H2B and H3. Histone H4 on the other hand is reported to exist as a single form (Tachiwana et al, 2011). It will be clear to those skilled in the art that an ELISA method of the invention using an antibody or binder targeted to bind to histone H4 will bind to virtually all nucleosomes in a sample. Thus in one embodiment the invention provides a novel method for the detection of nucleosomes per se in which nucleosomes containing a common histone variant are measured as a way of ensuring that all or most nucleotides are in fact detected. It will further be clear to those skilled in the art that suitable antibodies or ligands produced for this application may be targeted to regions of histone H4 that are not subject to PTM modification. This will further increase the universality of the selected epitope as an epitope common to all or most nucleosomes. Thus the present invention described provides a means to detect all or most nucleosomes in a sample despite the variation in constituent histone isoforms and PTMs.

It will further be clear that the method of the present invention can be developed to detect or measure any nucleic acid or DNA base in nucleosomes. Such bases include, without limitation adenine, thymine, guanine, cytosine, uracil, inosine, xanthine, hypoxanthine, 7,8-dihydro-8-oxo-guanine and any derivatives of these. It will be clear to those skilled in the art that a common nucleotide (for example without limitation; guanine, cytosine, thymine or adenine), will occur in all or most nucleosomes and that the method of the invention using an antibody to a common nucleotide will provide a method to bind and detect virtually all nucleosomes in a sample.

Thus in one embodiment the invention provides a novel method for the detection of nucleosomes per se in which nucleosomes containing a common nucleotide are measured as a way of ensuring that all or most nucleotides are in fact detected.

It will be clear to those skilled in the art that the term nucleotide herein is intended to include without limitation purines, pyrimidines or other nucleic acid bases and similar molecules with or without associated sugars and with or without phosphorylation.

The ELISA methods reported here can be used quickly and simply in multiple samples, for example blood samples. The methods of the invention can be used to detect and measure intact nucleosomes in any sample where such nucleosomes occur including, for example, samples obtained by digestion of chromatin extracted from cells. ELISA methods are rapid, low cost and suitable for use in complex biological media and fluids. It will be clear to those skilled in the art that a biomarker present in the blood samples taken from cancer patients has value for a broad range of diagnostic and disease screening purposes for cancer and other diseases which are associated with elevated circulating nucleosomes (Holdenrieder et al, 2001).

We measured nucleosomes containing the three histone variants, as well as the histone PTM P-H2AX(Ser139) and the nucleotides 5-methylcytosine and 5-hydroxymethylcytosine individually in the sera of 20 healthy subjects and in healthy bovine serum. The serum results for all six individual ELISA tests were all low or undetectable. We also conducted a similar test in plasma samples, taken from the same 20 healthy subjects, for five of the six ELISA methods of the invention and, surprisingly, higher signals were observed. This finding is unexpected and quite different from the results we found for nucleosome ELISA methods of the current art.

The finding that nucleosomes are present in blood samples taken from subjects with cancer which are found to have no nucleosomes by current nucleosome ELISA methods may indicate that antibodies used in current methods are directed to epitopes which are not universally present in circulating nucleosomes or are masked or otherwise unavailable for antibody binding. In order to overcome this problem and produce ELISA methods which detect all or most nucleosomes, we have designed and demonstrated a novel nucleosome ELISA in which the capture antibody is an anti-histone antibody and the detection antibody reagent used is a mixture of multiple detection antibodies including an anti-macroH2A2 antibody, an anti-h2AZ antibody and an anti-thymine antibody. Whereas individual ELISA methods for histone variants detect little or no circulating nucleosomes in 3 lung cancer subjects we tested, this novel nucleosome ELISA detects the presence of circulating nucleosomes in all 3 cancer subjects. It will be clear to those skilled in the art that the particular combination of antibodies employed in this ELISA method of the invention is not limiting and that more or fewer antibodies could be employed. In general, increasing the number of antibodies employed which are directed at different nucleosome epitopes may increase the range of nucleosomes that are detected by the assay. However, the optimal use of antibodies will be constrained by increasing background, or non-specific binding effects, caused by increasing detection antibody concentration.

It will be clear to those skilled in the art that whereas a monoclonal antibody is a single antibody molecular species and binds a unique epitope or to a narrow range of epitopes; polyclonal antibodies on the other hand represent a mixture of antibody molecules which bind a broader range of epitopes in the target immunogen used to raise the antibody. The nucleosome epitopes detected in a nucleosome immunoassay can therefore be increased by the use of a polyclonal antibody in place of one or both monoclonal antibodies employed in current nucleosome ELISA methods.

According to another aspect of the invention there is provided a new and novel nucleosome immunoassay in which the single capture antibody and/or the single detection antibody used in ELISA methods of the current art is replaced by two or multiple antibodies for either or both the capture and detection antibody reagents, so that a greater variety of nucleosomes is detected by the assay. A preferred embodiment of the invention involves the use of two or more or multiple capture antibodies and/or two or more or multiple detection antibodies where one or more of the said antibodies are anti-histone variant antibodies and/or anti histone modification antibodies and/or anti-nucleotide antibodies to detect nucleosomes not detected by current methods.

We developed an assay aimed at multiple nucleosome epitopes using an anti-histone capture antibody and a mixture of a biotinylated anti-mH2A2, a biotinylated anti-H2AZ and a biotinylated anti-thymine dimer antibody as detection antibody reagent. All of these antibodies failed to detect nucleosomes in the same 3 samples taken from cancer patients. We used this multiple epitope nucleosome ELISA method to test the same 3 samples. Surprisingly, nucleosomes were detectable in all 3 samples. This result indicates that multiple epitope nucleosome assays are better able to detect nucleosomes than individual nucleosome epitope assays.

According to one embodiment of the invention there is provided a method for detecting and measuring cell free nucleosomes in a sample by an immunoassay which comprises the steps of:
(i) contacting the sample which may contain nucleosomes with a first binding agent which binds to nucleosomes;
(ii) contacting the nucleosomes or sample with two or more second binding agents which bind to different or separate nucleosome epitopes;
(iii) detecting and/or quantifying the binding of said multiple second binding agents to nucleosomes in the sample; and
(iv) using the presence or degree of such binding as a measure of the presence of nucleosomes in the sample.

According to another embodiment of the invention there is provided a method for detecting and measuring cell free nucleosomes in a sample by an immunoassay which comprises the steps of:
(i) contacting the sample which may contain nucleosomes with two or more first binding agents which bind to different or separate nucleosome epitopes;
(ii) contacting the nucleosomes or sample with a second binding agent which binds to nucleosomes; and
(iii) detecting and/or quantifying the binding of said second binding agent to nucleosomes in the sample.

According to another embodiment of the invention there is provided a method for detecting and measuring cell free nucleosomes in a sample by an immunoassay which comprises the steps of:
(i) contacting the sample which may contain nucleosomes with two or more first binding agents which bind to different or separate nucleosome epitopes;
(ii) contacting the nucleosomes or sample with two or more second binding agents which bind to different or separate nucleosome epitopes;
(iii) detecting and/or quantifying the binding of said second binding agents to nucleosomes in the sample; and
(iv) using the presence or degree of such binding as a measure of the presence of nucleosomes in the sample.

In one embodiment, the binding agent comprises an antibody.

According to a another aspect of the invention there is provided a new and novel nucleosome immunoassay in which either or both of the single capture antibody and/or the single detection antibody in currently used nucleosome ELISA methods is replaced by an anti-nucleosome polyclonal antibody, so that a greater variety of nucleosomes is detected by the assay. It will be clear to those skilled in the art that such anti-nucleosome antibodies may be produced by a variety of methods including using disease model animals (Salgame et al, 1997) or immunizing animals with intact nucleosomes or conjugates of nucleosomes linked to a strongly immunogenic substance. Suitable nucleosome antigens for use directly as immunogens or for conjugation may be produced for example, without limitation, by extraction of chromatin from a cell or cells and breaking down the chromatin extract to produce mono-nucleosomes and/or oligo-nucleosomes. Methods for producing mono-nucleosomes and/or oligo-nucleosomes from chromatin are well known in the art and include enzyme digestion and sonication (Dai et al, 2011). Typically immunometric polyclonal assays of the art involve the purification of serum or plasma polyclonal antibodies to prepare pure immunoglobulin fractions using for example ammonium sulphate precipitation of immunoglobulins and/ or protein A or protein G immunoglobulin purification methods. In addition those antibody molecules directed only at the antigen of interest can be isolated by affinity purification. In one embodiment of the invention a labelled polyclonal antibody is used as the detection antibody. In another embodiment of the invention a purified polyclonal antibody is used as capture antibody in combination with a labelled purified polyclonal detection antibody. In a preferred embodiment of the invention a purified polyclonal antibody is used as capture antibody in combination with two or more or multiple (monoclonal or polyclonal) detection antibodies directed at different nucleosome epitopes. In a particularly preferred embodiment one or more of the said detection antibodies are anti-histone variant and/or anti-nucleotide and/or anti-histone PTM antibodies.

According to another aspect of the invention there is provided a method for detecting and measuring cell free nucleosomes in a sample by an immunoassay which comprises the steps of:
(i) contacting the sample with two or more binding agents directed to bind to different nucleosome epitopes;
(ii) detecting and/or quantifying the binding of said binding agents to nucleosomes in the sample; and
(iii) using the presence or degree of such binding as a measure of the presence of nucleosomes in the sample.

In one embodiment, the binding agent comprises an antibody.

It will be clear to those skilled in the art that the methods of the invention described include a variety of embodiments including classical competitive immunoassays as well as biosensor type assays and label-free assays of the type marketed for example by ForteBio Incorporated of USA.

According to another aspect of the invention there is provided a method for detecting or diagnosing the presence of a disease by measuring or detecting the presence and/or the level or concentration of cell free nucleosomes in a body fluid, and using the detected level as a biomarker of the disease status of a subject. It will be appreciated by those skilled in the art that body fluids used for diagnostic testing include without limitation blood, serum, plasma, urine, cerebrospinal fluid and other fluids. In a preferred embodiment the body fluid selected as the sample is blood, serum or plasma.

According to a further aspect of the invention there is provided a method for detecting or measuring the presence of nucleosomes in a cell extract which comprises the steps of:
(i) isolating chromatin from a cell;
(ii) digesting sonicating or otherwise breaking down the chromatin to form mono-nucleosomes and/or oligo-nucleosomes; and
(iii) detecting or measuring the presence of nucleosomes in the digest by means of an immunoassay method of the invention.

It will be clear to those skilled in the art that the terms antibody, binder or ligand in regard to any aspect of the invention is not limiting but intended to include any binder capable of binding to specific molecules or entities and that any suitable binder can be used in the method of the invention. It will also be clear that the term nucleosomes is intended to include mononucleosomes and oligonucleosomes and any such chromatin fragments that can be analysed in fluid media.

According to another aspect of the invention there is provided a kit for detecting or measuring nucleosomes which comprises multiple capture and/or detection ligands or binders specific for a nucleotide or histone variant or histone PTM or a component part thereof, or a structural/shape mimic of the nucleosome or component part thereof, together with instructions for use of the kit in accordance with any of the methods defined herein.

According to a further aspect of the invention there is provided a kit for detecting or measuring nucleosomes containing two or more epitopes including a histone variant or histone PTM or nucleotide which comprises two or more capture and/or two or more detection ligands or binders specific for a histone variant or histone PTM or nucleotide or a component part thereof, or a structural/shape mimic of the nucleosome or component part thereof, together with instructions for use of the kit in accordance with any of the methods defined herein.

A further aspect of the invention provides ligands or binders, such as naturally occurring or chemically synthesised compounds, capable of specific binding to the biomarker. A ligand or binder according to the invention may comprise a peptide, an antibody or a fragment thereof, or a synthetic ligand such as a plastic antibody, or an aptamer or oligonucleotide, capable of specific binding to the biomarker. The antibody can be a monoclonal antibody or a fragment thereof capable of specific binding to the biomarker. A ligand according to the invention may be labeled with a detectable marker, such as a luminescent, fluorescent, enzyme or radioactive marker; alternatively or additionally a ligand according to the invention may be labelled with an affinity tag, e.g. a biotin, avidin, streptavidin or His (e.g. hexa-His) tag. Alternatively ligand binding may be determined using a label-free technology for example that of ForteBio Inc.

A biosensor according to the invention may comprise the biomarker or a structural/shape mimic thereof capable of specific binding to an antibody against the biomarker. Also provided is an array comprising a ligand or mimic as described herein.

Also provided by the invention is the use of one or more ligands as described herein, which may be naturally occurring or chemically synthesised, and is suitably a peptide, antibody or fragment thereof, aptamer or oligonucleotide, or the use of a biosensor of the invention, or an array of the invention, or a kit of the invention to detect and/or quantify the biomarker. In these uses, the detection and/or quantification can be performed on a biological sample as defined herein.

Diagnostic or monitoring kits are provided for performing methods of the invention. Such kits will suitably comprise a ligand according to the invention, for detection and/or quantification of the biomarker, and/or a biosensor, and/or an array as described herein, optionally together with instructions for use of the kit.

A further aspect of the invention is a kit for detecting the presence of a disease state, comprising a biosensor capable of detecting and/or quantifying one or more of the biomarkers as defined herein.

Biomarkers for detecting the presence of a disease are essential targets for discovery of novel targets and drug molecules that retard or halt progression of the disorder. As the level of the biomarker is indicative of disorder and of drug response, the biomarker is useful for identification of novel therapeutic compounds in in vitro and/or in vivo assays. Biomarkers of the invention can be employed in methods for screening for compounds that modulate the activity of the biomarker.

Thus, in a further aspect of the invention, there is provided the use of a binder or ligand, as described, which can be a peptide, antibody or fragment thereof or aptamer or oligonucleotide according to the invention; or the use of a biosensor according to the invention, or an array according to the invention; or a kit according to the invention, to identify a substance capable of promoting and/or of suppressing the generation of the biomarker.

Also there is provided a method of identifying a substance capable of promoting or suppressing the generation of the biomarker in a subject, comprising administering a test substance to a subject animal and detecting and/or quantifying the level of the biomarker present in a test sample from the subject.

The term "biomarker" means a distinctive biological or biologically derived indicator of a process, event, or condition. Biomarkers can be used in methods of diagnosis, e.g. clinical screening, and prognosis assessment and in monitoring the results of therapy, identifying patients most likely to respond to a particular therapeutic treatment, drug screening and development. Biomarkers and uses thereof are valuable for identification of new drug treatments and for discovery of new targets for drug treatment.

The terms "detecting" and "diagnosing" as used herein encompass identification, confirmation, and/or characterisation of a disease state. Methods of detecting, monitoring and of diagnosis according to the invention are useful to confirm the existence of a disease, to monitor development of the disease by assessing onset and progression, or to assess amelioration or regression of the disease. Methods of detecting, monitoring and of diagnosis are also useful in methods for assessment of clinical screening, prognosis, choice of therapy, evaluation of therapeutic benefit, i.e. for drug screening and drug development.

Efficient diagnosis and monitoring methods provide very powerful "patient solutions" with the potential for improved prognosis, by establishing the correct diagnosis, allowing rapid identification of the most appropriate treatment (thus lessening unnecessary exposure to harmful drug side effects), and reducing relapse rates.

In one embodiment, said biomarker is released from the cells of a tumour. Thus, according to a further aspect of the invention there is provided a method for the detection of a tumour growth which comprises the steps of (i) measuring a biomarker in a biological sample that is associated with or released from the cells of a tumour and (ii) demonstrating that the level of said biomarker is associated with the size, stage, aggressiveness or dissemination of the tumour.

It is known that increased cell turnover, cell death and apoptosis lead to increased circulatory levels of cell free nucleosomes (Holdenrieder et al, 2001). Circulating cell free nucleosomes level is a non-specific indicator and occurs in a variety of conditions including inflammatory diseases, a large variety of benign and malignant conditions, autoimmune diseases, as well as following trauma or ischaemia (Holdenrieder et a/2001). It will be clear to those skilled in the art that the invention will have application in a variety of disease areas where circulating nucleosomes have been found in subjects. These include, without limitation, trauma (for example; severe injury or surgery), extreme exercise (for example running a marathon), stroke and heart attack, sepsis or other serious infection and endometriosis. As methods of the current invention are capable of detection of a wider range of nucleosomes than current nucleosome ELISA methods, applications in further disease areas may be found.

The immunoassays of the invention include immunometric assays employing enzyme detection methods (for example ELISA), fluorescence labelled immunometric assays, time-resolved fluorescence labelled immunometric assays, chemiluminescent immunometric assays, immunoturbidimetric assays, particulate labelled immunometric assays and immunoradiometric assays and competitive immunoassay methods including labelled antigen and labelled antibody competitive immunoassay methods with a variety of label types including radioactive, enzyme, fluorescent, time-resolved fluorescent and particulate labels. All of said immunoassay methods are well known in the art, see for example Salgame et al, 1997 and van Nieuwenhuijze et al, 2003.

In one embodiment, said biological sample comprises a body fluid. For example, biological samples that may be tested in a method of the invention include cerebrospinal fluid (CSF), whole blood, blood serum, plasma, menstrual blood, endometrial fluid, urine, saliva, or other bodily fluid (stool, tear fluid, synovial fluid, sputum), breath, e.g. as condensed breath, or an extract or purification therefrom, or dilution thereof. Biological samples also include specimens from a live subject, or taken post-mortem. The samples can be prepared, for example where appropriate diluted or concentrated, and stored in the usual manner.

In one embodiment, the method of the invention is repeated on multiple occasions. This embodiment provides the advantage of allowing the detection results to be monitored over a time period. Such an arrangement will provide the benefit of monitoring or assessing the efficacy of treatment of a disease state. Such monitoring methods of the invention can be used to monitor onset, progression, stabilisation, amelioration, relapse and/or remission.

Thus, the invention also provides a method of monitoring efficacy of a therapy for a disease state in a subject, suspected of having such a disease, comprising detecting and/or quantifying the biomarker present in a biological sample from said subject. In monitoring methods, test samples may be taken on two or more occasions. The method may further comprise comparing the level of the biomarker(s) present in the test sample with one or more control(s) and/or with one or more previous test sample(s) taken earlier from the same test subject, e.g. prior to commencement of therapy, and/or from the same test subject at an earlier stage of therapy. The method may comprise detecting a change in the nature or amount of the biomarker(s) in test samples taken on different occasions.

Thus, according to a further aspect of the invention, there is provided a method for monitoring efficacy of therapy for a disease state in a human or animal subject, comprising:
(i) quantifying the amount of the biomarker as defined herein; and
(ii) comparing the amount of said biomarker in a test sample with the amount present in one or more control(s) and/or one or more previous test sample(s) taken at an earlier time from the same test subject.

A change in the level of the biomarker in the test sample relative to the level in a previous test sample taken earlier from the same test subject may be indicative of a beneficial effect, e.g. stabilisation or improvement, of said therapy on the disorder or suspected disorder. Furthermore, once treatment has been completed, the method of the invention may be periodically repeated in order to monitor for the recurrence of a disease.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

In a further embodiment the monitoring of more rapid changes due to fast acting therapies may be conducted at shorter intervals of hours or days.

According to a further aspect of the invention, there is provided a method for identifying a biomarker for detecting the presence of a disease state. The term "identifying" as used herein means confirming the presence of the biomarker present in the biological sample. Quantifying the amount of the biomarker present in a sample may include determining the concentration of the biomarker present in the sample. Identifying and/or quantifying may be performed directly on the sample, or indirectly on an extract therefrom, or on a dilution thereof.

In alternative aspects of the invention, the presence of the biomarker is assessed by detecting and/or quantifying antibody or fragments thereof capable of specific binding to the biomarker that are generated by the subject's body in response to the biomarker and thus are present in a biological sample from a subject having a disease state.

Identifying and/or quantifying can be performed by any method suitable to identify the presence and/or amount of a specific protein in a biological sample from a patient or a purification or extract of a biological sample or a dilution thereof. In methods of the invention, quantifying may be performed by measuring the concentration of the biomarker in the sample or samples. Biological samples that may be tested in a method of the invention include those as defined hereinbefore. The samples can be prepared, for example where appropriate diluted or concentrated, and stored in the usual manner.

Identification and/or quantification of biomarkers may be performed by detection of the biomarker or of a fragment thereof, e.g. a fragment with C-terminal truncation, or with N-terminal truncation. Fragments are suitably greater than 4 amino acids in length, for example 5, 6, 7, 8, 9, 10, 11, 12, 13, 14, 15, 16, 17, 18, 19, or 20 amino acids in length. It is noted in particular that peptides of the same or related sequence to that of histone tails are particularly useful fragments of histone proteins.

The biomarker may be directly detected, e.g. by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, or oligonucleotide, capable of specifically binding the biomarker. The ligand or binder may possess a detectable label, such as a luminescent, fluorescent or radioactive label, and/or an affinity tag.

For example, detecting and/or quantifying can be performed by one or more method(s) selected from the group consisting of: SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC MS-based techniques. Appropriate LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods of diagnosing or monitoring according to the invention may comprise analysing a sample by SELDI TOF or MALDI TOF to detect the presence or level of the biomarker. These methods are also suitable for clinical screening, prognosis, monitoring the results of therapy, identifying patients most likely to respond to a particular therapeutic treatment, for drug screening and development, and identification of new targets for drug treatment.

Identifying and/or quantifying the analyte biomarkers may be performed using an immunological method, involving an antibody, or a fragment thereof capable of specific binding to the biomarker. Suitable immunological methods include sandwich immunoassays, such as sandwich ELISA, in which the detection of the analyte biomarkers is performed using two antibodies which recognize different epitopes on a analyte biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g. using gold, silver, or latex particles, magnetic particles, or Q-dots). Immunological methods may be performed, for example, in microtitre plate or strip format.

According to a further aspect of the invention, there is provided a biomarker identified by the method as defined herein.

In one embodiment, one or more of the biomarkers may be replaced by a molecule, or a measurable fragment of the molecule, found upstream or downstream of the biomarker in a biological pathway.

The identification of key biomarkers specific to a disease is central to integration of diagnostic procedures and therapeutic regimes. Using predictive biomarkers appropriate diagnostic tools such as biosensors can be developed; accordingly, in methods and uses of the invention, identifying and quantifying can be performed using a biosensor, microanalytical system, microengineered system, microseparation system, immunochromatography system or other suitable analytical devices. The biosensor may incorporate an immunological method for detection of the biomarker(s), electrical, thermal, magnetic, optical (e.g. hologram) or acoustic technologies. Using such biosensors, it is possible to detect the target biomarker(s) at the anticipated concentrations found in biological samples.

As used herein, the term "biosensor" means anything capable of detecting the presence of the biomarker. Examples of biosensors are described herein.

Biosensors according to the invention may comprise a ligand binder or ligands, as described herein, capable of specific binding to the biomarker. Such biosensors are useful in detecting and/or quantifying a biomarker of the invention.

The biomarker(s) of the invention can be detected using a biosensor incorporating technologies based on "smart" holograms, or high frequency acoustic systems, such systems are particularly amenable to "bar code" or array configurations.

In smart hologram sensors (Smart Holograms Ltd, Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment. A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of one or more biomarkers of the invention combine biomolecular recognition with appropriate means to convert detection of the presence, or quantitation, of the biomarker in the sample into a signal.

Biosensors can be adapted for "alternate site" diagnostic testing, e.g. in the ward, outpatients' department, surgery, home, field and workplace.

Biosensors to detect one or more biomarkers of the invention include acoustic, plasmon resonance, holographic, Bio-Layer Interferometry (BLI) and microengineered sensors. Imprinted recognition elements, thin film transistor technology, magnetic acoustic resonator devices and other novel acousto-electrical systems may be employed in biosensors for detection of the one or more biomarkers of the invention.

Methods involving identification and/or quantification of one or more biomarkers of the invention can be performed on bench-top instruments, or can be incorporated onto disposable, diagnostic or monitoring platforms that can be used in a non-laboratory environment, e.g. in the physician's office or at the patient's bedside. Suitable biosensors for performing methods of the invention include "credit" cards with optical or acoustic readers. Biosensors can be configured to allow the data collected to be electronically transmitted to the physician for interpretation and thus can form the basis for e-medicine.

Diagnostic kits for the diagnosis and monitoring of the presence of a disease state are described herein. In one embodiment, the kits additionally contain a biosensor capable of identifying and/or quantifying a biomarker. Suitably a kit according to the invention may contain one or more components selected from the group: a ligand binder, or ligands, specific for the biomarker or a structural/shape mimic of the biomarker, one or more controls, one or more reagents and one or more consumables; optionally together with instructions for use of the kit in accordance with any of the methods defined herein.

The identification of biomarkers for a disease state permits integration of diagnostic procedures and therapeutic regimes. Detection of a biomarker of the invention can be used to screen subjects prior to their participation in clinical trials. The biomarkers provide the means to indicate therapeutic response, failure to respond, unfavourable side-effect profile, degree of medication compliance and achievement of adequate serum drug levels. The biomarkers may be used to provide warning of adverse drug response. Biomarkers are useful in development of personalized therapies, as assessment of response can be used to fine-tune dosage, minimise the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

Biomarker-based tests provide a first line assessment of 'new' patients, and provide objective measures for accurate and rapid diagnosis, not achievable using the current measures.

Furthermore, diagnostic biomarker tests are useful to identify family members or patients with mild or asymptomatic disease or who may be at high risk of developing symptomatic disease. This permits initiation of appropriate therapy, or preventive measures, e.g. managing risk factors. These approaches are recognised to improve outcome and may prevent overt onset of the disorder.

Biomarker monitoring methods, biosensors and kits are also vital as patient monitoring tools, to enable the physician to determine whether relapse is due to worsening of the disorder. If pharmacological treatment is assessed to be inadequate, then therapy can be reinstated or increased; a change in therapy can be given if appropriate. As the biomarkers are sensitive to the state of the disorder, they provide an indication of the impact of drug therapy.

The invention will now be illustrated with reference to the following non-limiting examples.

EXAMPLE 1

A nucleosome preparation (produced either by digestion of chromatin extracted from cancer cell lines or produced according to the method of *Holdenrieder et al, 2001) was serially diluted into fetal calf serum and assayed using individual ELISA methods for the nucleosome associated histone variants mH2A1.1, mH2A2, H2AZ and the nucleosome associated nucleotides 5-methylcytosine, 5-hydroxymethylcytosine and thymine and the nucleosome associated PTM P-H2AX(Ser139) using a solid phase anti-histone capture antibody that binds intact nucleosomes and does not bind histone H2 and an appropriate biotinylated anti-histone variant or anti-histone PTM or anti-nucleotide detection antibody. Neat fetal calf serum was also run in the ELISA as a control sample containing no cell free nucleosomes. The assay method was as follows: A solution of anti-histone antibody in 0.1 M phosphate buffer pH 7.4 was added to microtitre wells (100 µL/well) and incubated overnight at 4° C. to coat the wells with capture antibody. Excess anti-histone antibody was decanted. A solution of bovine serum albumin (20 g/L) was added to the wells (200 µL/well) and incubated at room temperature to block excess protein binding sites on the wells. Excess bovine serum albumin solution was decanted and the wells were washed three times with wash buffer (200 µL/well, 0.05M TRIS/HCl buffer pH 7.5 containing 1% Tween 20). Sample (10 µL/well) and assay buffer (50 µL/well, 0.05M TRIS/HCl pH 7.5 containing 0.9% NaCl, 0.05% sodium deoxycholate and 1% Nonidet P40 substitute) were added to the wells and incubated. The sample and assay buffer mixture was decanted and the wells were washed three times with wash buffer (200 µL/well). A solution of biotinylated anti-histone variant or histone PTM or nucleotide detection antibody was added (50 µL/well) and incubated. Excess detection antibody was decanted and the wells were again washed three times with wash buffer (200 µL/well). A solution containing a streptavidin-horse radish peroxidase conjugate was added (50 µL/well) and incubated. Excess conjugate was decanted and the wells were again washed three times with wash buffer (200 µL/well). A coloured substrate solution (100 µL/well, 2,2'-Azinobis[3-ethylbenzothiazoline-6-sulfonic acid]-diammonium salt) was added and incubated 20 minutes at room temperature with mild agitation. The optical density (OD) of the wells was measured at a wavelength of 405 nm using a standard microtitre plate reader. A dose response curve of increasing colour with increasing individual nucleosome associated histone variant or histone PTM or nucleotide concentration was observed with a low background signal observed in the absence of histone variant, histone PTM or nucleotide (fetal calf serum). The results are shown in FIGS. 1, 2, 3, 4, 5, 6 and 7.

EXAMPLE 2

We used two nucleosome ELISA methods of the current art to measure the circulating cell free nucleosome content of serum and plasma blood samples taken from 20 healthy subjects. The first current ELISA method (ELISA 1) was the Roche Cell Death ELISA and the other (ELISA 2) an ELISA employing a monoclonal anti-histone capture antibody and a monoclonal anti-histone-DNA complex detection antibody.

The nucleosome levels detected by both current nucleosome ELISA methods were lower in normal plasma than in normal serum.

We also measured the individual levels of nucleosomes containing three nucleosome associated histone variants, a histone PTM and a nucleotide in the same samples. The results showed that the serum samples taken from healthy subjects have uniformly low levels of nucleosomes containing histone variants or PTM or nucleotides. The measured plasma results were higher for all 20 healthy subjects. Thus the results for the method of the invention (plasma higher than serum) are different to those of the methods of the current art (serum higher than plasma). The results are shown in FIG. 14.

EXAMPLE 3

We used two nucleosome ELISA methods of the current art to measure the circulating cell free nucleosome content of plasma samples taken from 3 subjects with colon cancer, 13 subjects with lung cancer, 2 subjects with pancreatic cancer, 1 subject with oral cancer and a nucleosome sample produced from healthy subjects according to method of Holdenrieder (*Holdenrieder et al, 2001). The first current ELISA method (ELISA 1) was the Roche Cell Death ELISA and the other (ELISA 2) an ELISA employing a monoclonal anti-histone capture antibody and a monoclonal anti-histone-DNA complex detection antibody.

We also individually measured the levels of nucleosomes containing a number of variant histones, a histone PTM and two nucleotides. The results show that many samples taken from cancer subjects have low or undetectable nucleosome levels as determined by current nucleosome ELISA methods. However, most of these samples have detectable levels of nucleosomes that contain one or more nucleosome associated variant histones and nucleosome associated 5-hydroxymethylcytosine. All the samples were found to contain detectable levels of nucleosome associated 5-methylcytosine. The results are shown in FIGS. 10-13.

EXAMPLE 4

Figure 1:
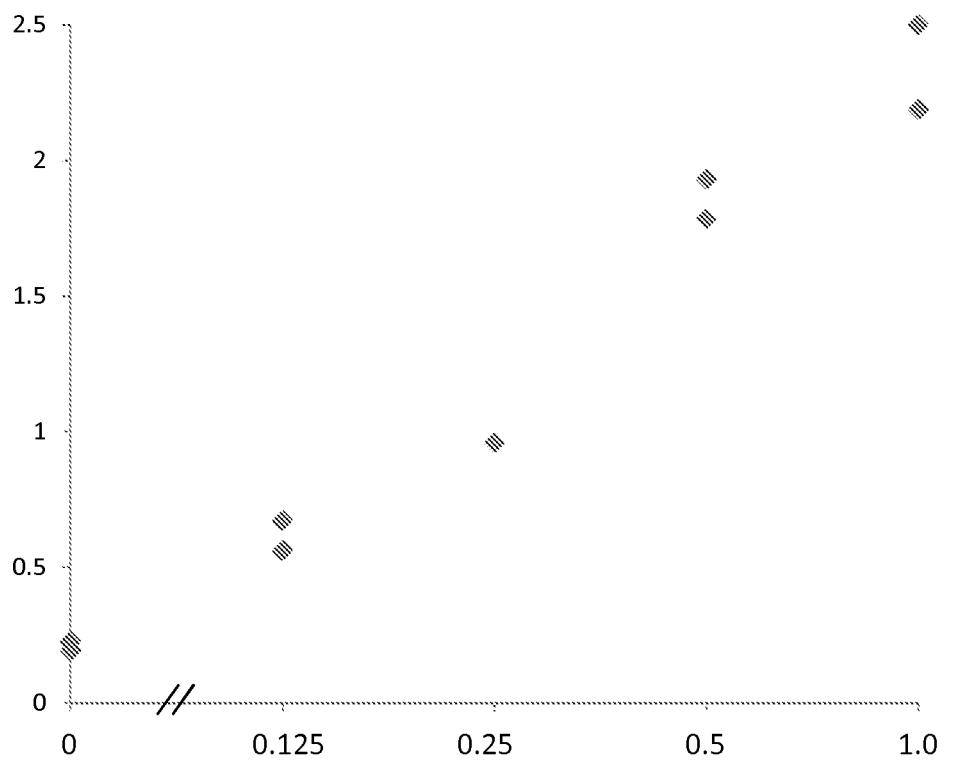
FIG. 1. ELISA dose response curve for the detection of histone variant macroH2A1.1 in a human cell free nucleosome preparation produced by the method of *Holdenrieder et al, 2001 diluted into calf serum.
Figure 2:
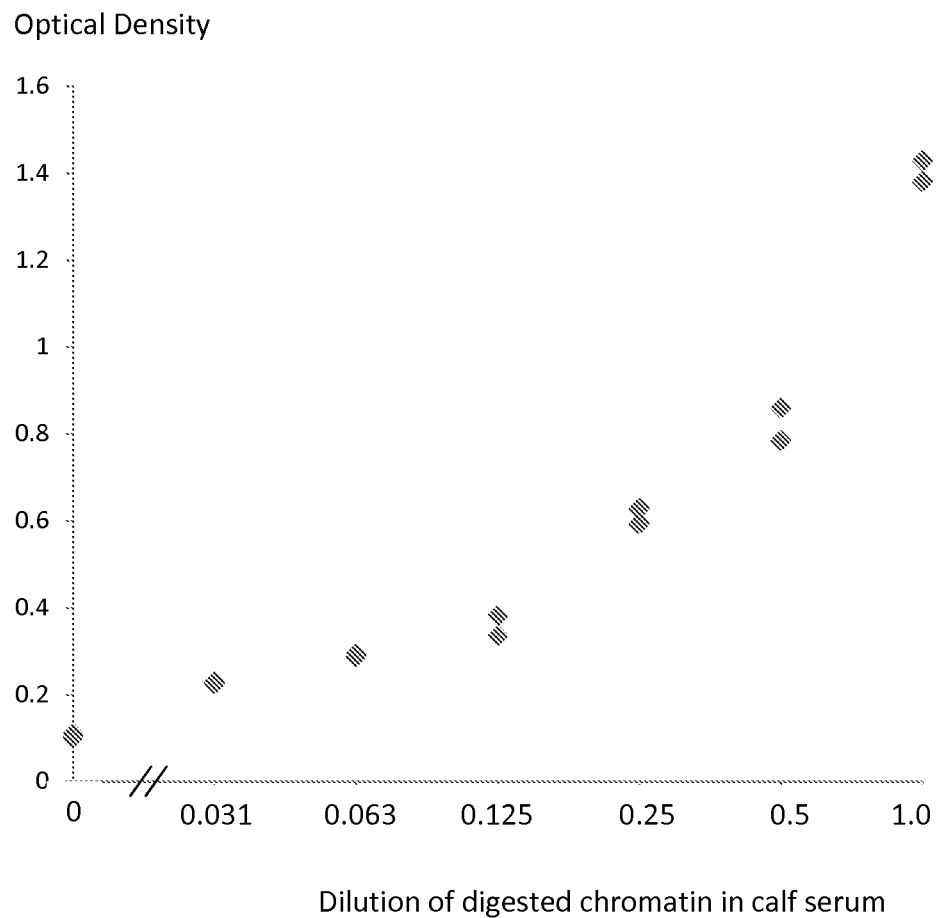
FIG. 2. ELISA dose response curve for the detection of histone variant macroH2A2 in cell free nucleosomes in cross-linked digested chromatin extracted from MCF7 cells diluted into calf serum.
Figure 3:
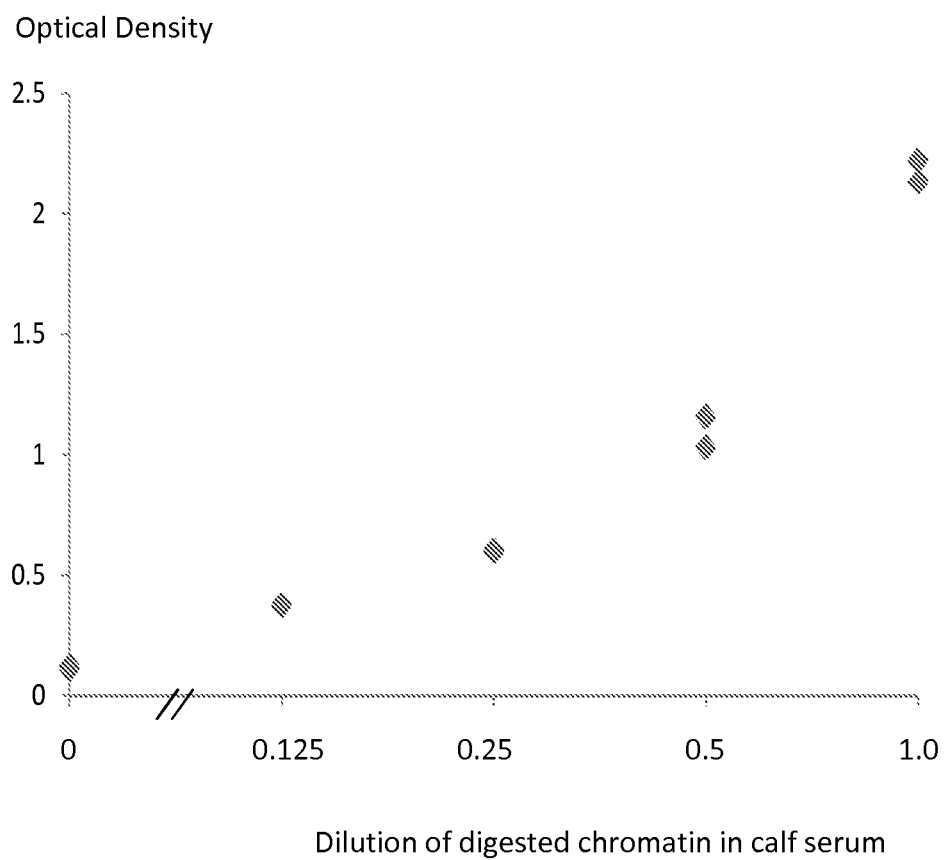
FIG. 3. ELISA dose response curve for the detection of histone variant H2AZ in cell free nucleosomes in cross-linked digested chromatin extracted from MCF7 cells diluted into calf serum.
Figure 4:
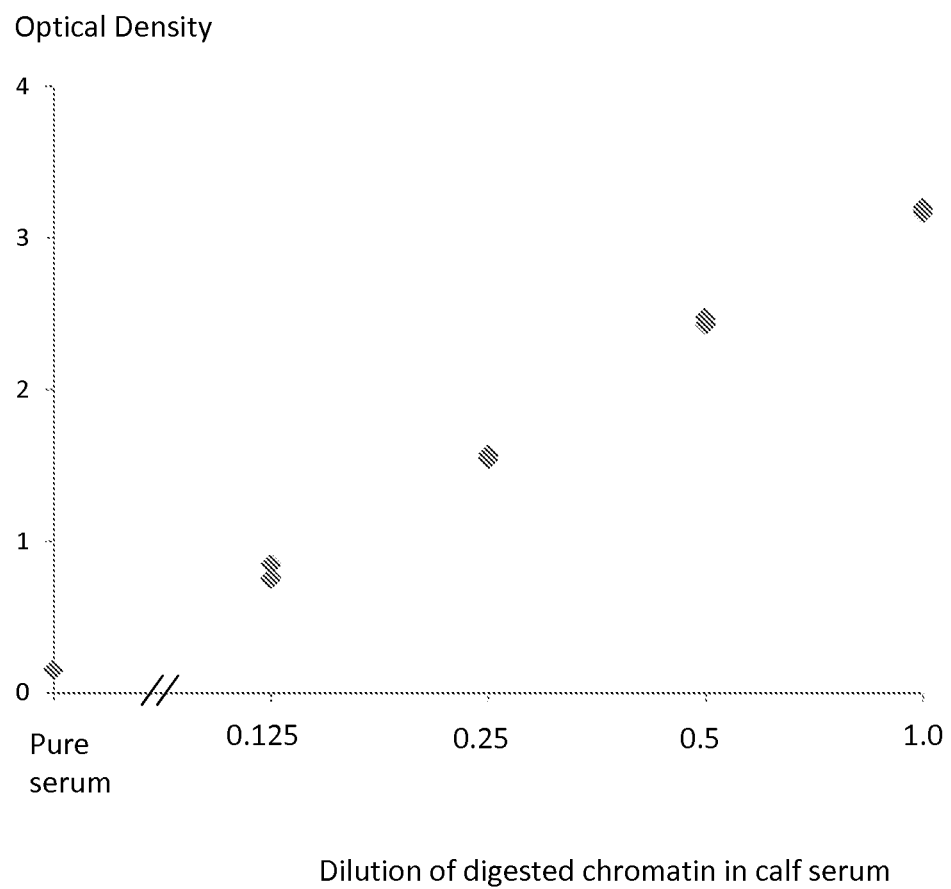
FIG. 4. ELISA dose response curve for the detection of 5-methylcytosine methylated DNA in cell free nucleosomes in cross-linked digested chromatin extracted from MCF7 cells diluted into calf serum.
Figure 5:
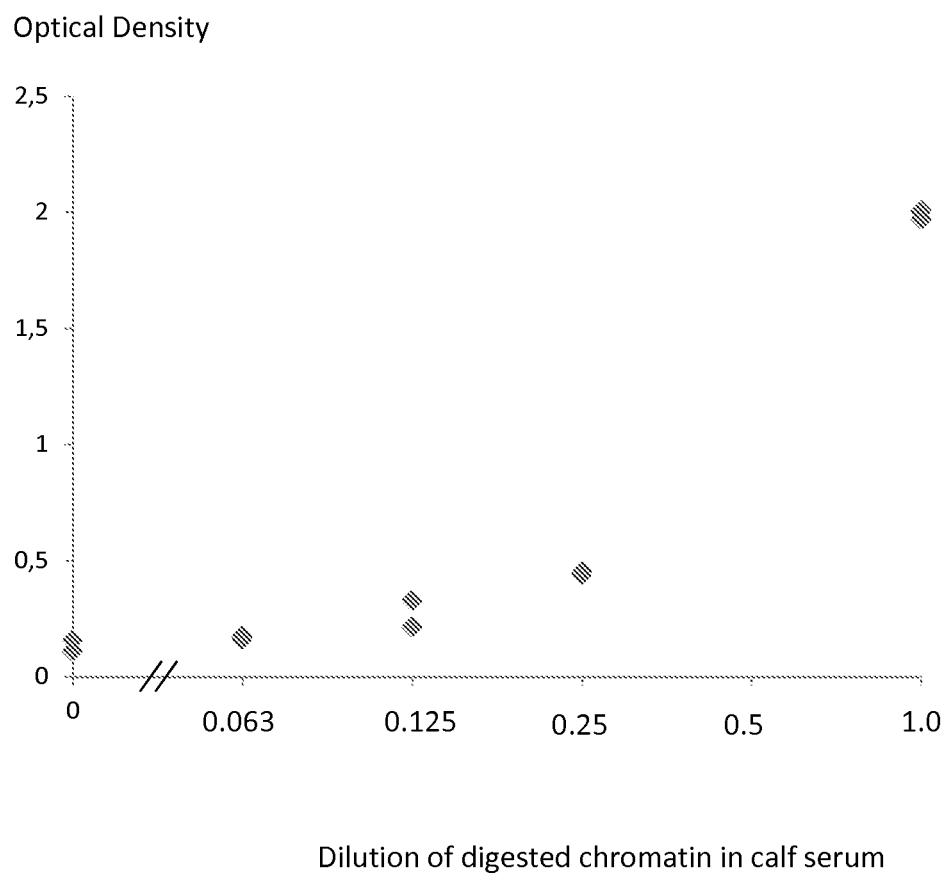
FIG. 5. ELISA dose response curve for the detection of 5-hydroxymethylcytosine methylated DNA in cell free nucleosomes in cross-linked digested chromatin extracted from A375 cells diluted into calf serum.
Figure 6:
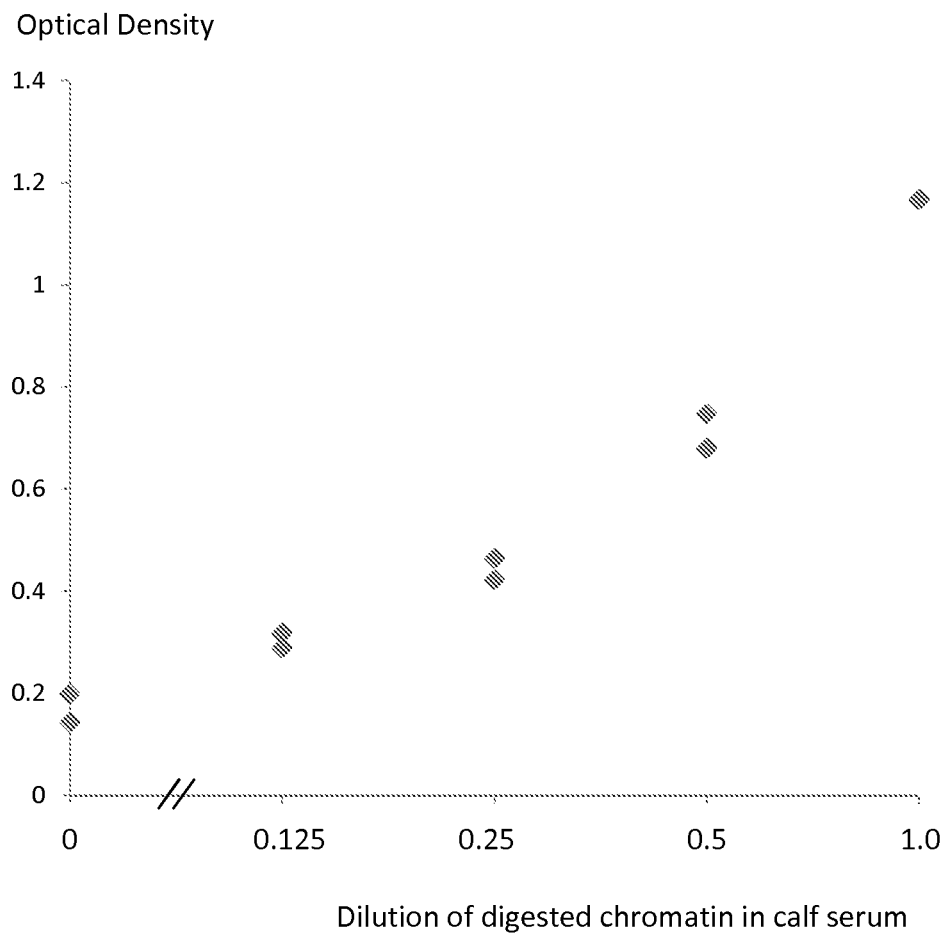
FIG. 6. ELISA dose response curve for the detection of thymine in cell free nucleosomes in cross-linked digested chromatin extracted from Hela cells diluted into calf serum.
Figure 7:
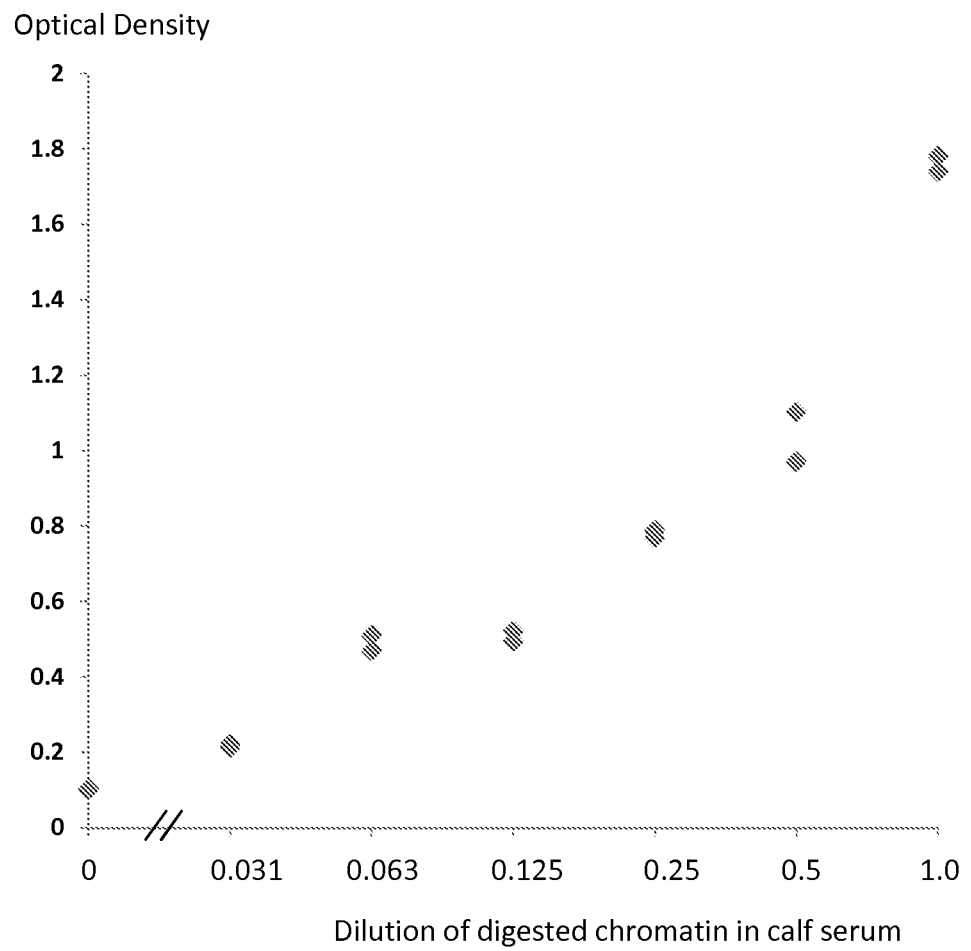
FIG. 7. ELISA dose response curve for the detection of phosphorylated Serine 139 H2AX in cell free nucleosomes in cross-linked digested chromatin extracted from MCF7 cells diluted into calf serum.
Figure 8:
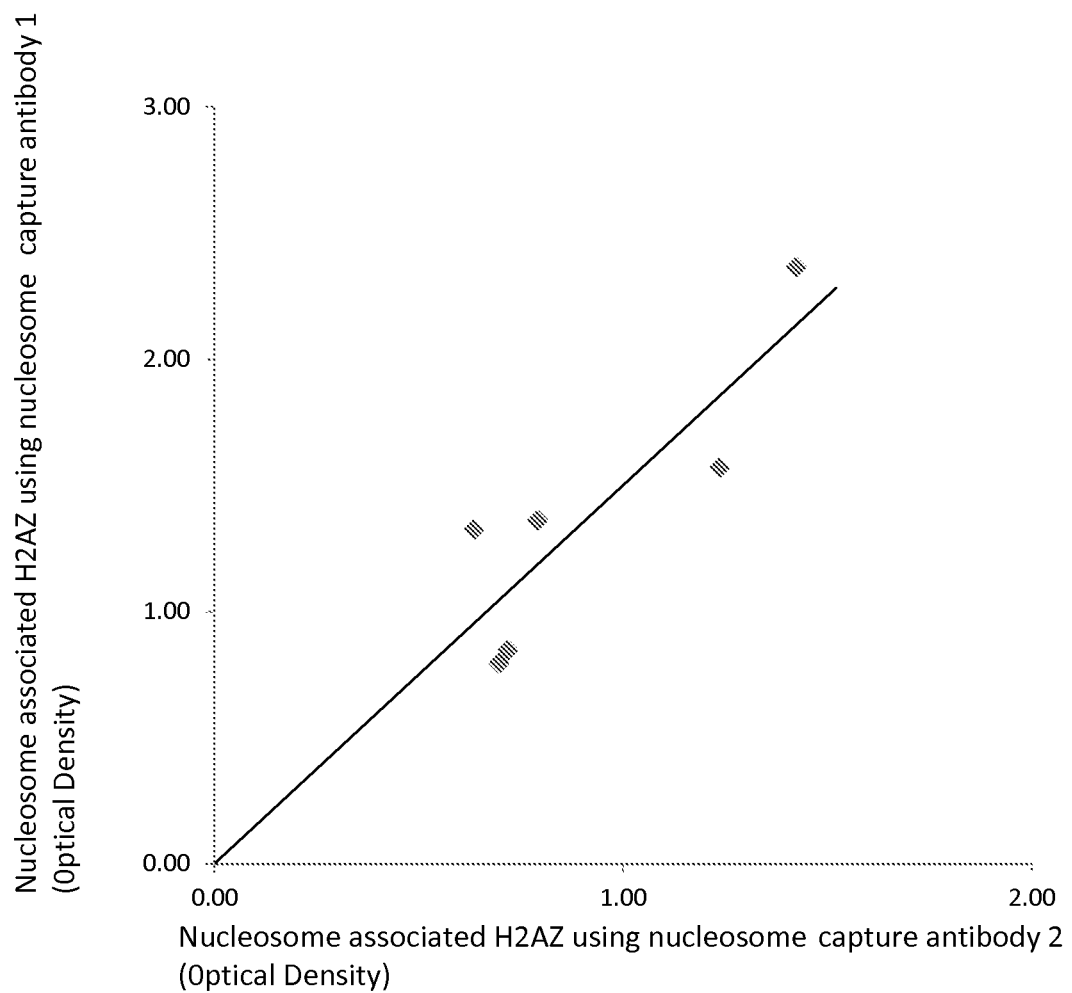
FIG. 8. Nucleosome associated histone H2AZ levels of human plasma samples taken from cancer patients measured using a biotinylated anti-H2AZ detection antibody with two different monoclonal clonal anti-histone capture antibodies.

We measured the nucleosome associated histone H2AZ levels of some human plasma samples taken from cancer patients using a biotinylated anti-H2AZ detection antibody. The method was performed twice using two different monoclonal anti-histone capture antibodies to determine if the H2AZ results were repeatable for different capture antibodies. The results in FIG. 8 show that the nucleosome associated histone H2AZ levels of the two assays are linearly related with an intercepts at approximately zero. The units are simple optical density readings.

EXAMPLE 5

A sample containing nucleosomes is analysed for nucleosome content using the method of the invention using a mixture of detection antibodies. The detection antibodies are selected to include antibodies directed at a diverse mixture of nucleosome epitopes; for example to include at least one anti-nucleotide antibody directed to a commonly occurring nucleotide and/or at least one anti-histone variant antibody directed to a commonly occurring histone isoform in order to target a number of distinct nucleosome epitopes that are likely to occur on all or most or large proportion of nucleosomes to enlarge the range of nucleosomes detected by the assay.

A multiple epitope nucleosome ELISA method was conducted using a mixture of biotinylated anti-mH2A2, biotinylated anti-H2AZ and biotinylated anti-thymine dimer antibodies as a detection antibody reagent mix following a method similar to that described in Example 1 above. We measured the nucleosome levels of the nucleosome blood sample prepared from healthy subjects as well as the 3 human blood samples taken from lung cancer patients in which nucleosome levels were very low or undetectable using each of the individual assays. Surprisingly nucleosomes were found to be detectable in all 3 samples with a significant signal/noise ratio that was greater than that for the individual assays or for a nucleosome ELISA of the current art. This indicates that the multiple epitope nucleosome ELISA method of the invention is a better detection method for the presence of cancer than methods of the current art. The results are shown in FIG. 9.

EXAMPLE 6

A sample containing nucleosomes is analysed for nucleosome content using the method of the invention using a mixture of two or more capture antibodies with one or more anti-nucleosome detection antibodies. The capture antibodies are selected to target a diverse selection of nucleosomes epitopes; for example to include at least one anti-nucleotide antibody directed to a commonly occurring nucleotide that is likely to be present in all or many or most nucleosomes and/or at least one anti-histone variant antibody directed to a commonly occurring histone isoform that is likely to be present in all or many or most nucleosomes in order to target a number of distinct nucleosome epitopes that are likely to occur on all or many or most nucleosomes to enlarge the range of nucleosomes detected by the assay.

EXAMPLE 7

A sample containing nucleosomes is analysed for nucleosome content using the method of the invention using a mixture of detection antibodies. The detection antibodies are selected to target a diverse selection of nucleosome epitopes; for example to include at least one anti-nucleotide antibody directed to a commonly occurring nucleotide that is likely to be present in all or many or most nucleosomes and/or at least one anti-histone variant antibody directed to a commonly occurring histone isoform that is likely to be present in all or many or most nucleosomes and/or at least one anti-histone modification antibody directed to a commonly occurring histone modification that is likely to be present in all or many or most nucleosomes in order to target a number of distinct nucleosome epitopes that are likely to occur on all or many or most nucleosomes to enlarge the range of nucleosomes detected by the assay.

EXAMPLE 8

A sample containing nucleosomes is analysed for nucleosome content using the method of the invention using a mixture of 2 or more capture antibodies and 2 or more anti-nucleosomes detection antibodies selected to target a diverse selection of nucleosome epitopes. The capture antibodies are selected to include at least one anti-nucleotide antibody directed to a commonly occurring nucleotide that is likely to be present in all or many or most nucleosomes and/or at least one anti-histone variant antibody directed to a commonly occurring histone isoform that is likely to be present in all or many or most nucleosomes and/or at least one anti-histone modification antibody directed to a commonly occurring histone modification that is likely to be present in all or many or most nucleosomes in order to target a number of distinct nucleosome epitopes that are likely to occur on all or most nucleosomes to enlarge the range of nucleosomes detected by the assay.

EXAMPLE 9

A sample containing nucleosomes is analysed for nucleosome content using the method of the invention using one or more polyclonal anti-nucleosome capture antibodies and/or one or more polyclonal anti-nucleosome detection antibodies in order to target a number of distinct nucleosome epitopes to enlarge the range of nucleosomes detected by the assay.

REFERENCES

Allen et al, A simple method for estimating global DNA methylation using bisulfite PCR of repetitive DNA elements. Nucleic Acids Research: 32(3) e38DOI: 10.1093/narignh032

Bawden et al, Detection of histone modification in cell-free nucleosomes. WO 2005/019826, 2005

Boulard et al, Histone variant macroH2A1 deletion in mice causes female-specific steatosis. Epigenetics & Chromatin: 3(8), 1-13, 2010 Cell Biolabs, Inc. Product Manual for "Global DNA Methylation ELISA Kit (5'-methyl-2'-deoxycytidine Quantitation", 2011

Dai et al, Detection of Post-translational Modifications on Native Intact Nucleosomes by ELISA. http://www.jove.com/details.php?id=2593 doi: 10.3791/2593. J Vis Exp. 50 (2011).

Deligezer et al, Sequence-Specific Histone Methylation Is Detectable on Circulating Nucleosomes in Plasma. Clinical Chemistry 54(7), 1125-1131, 2008 Epigentek Group Inc, Methylamp™ Global DNA Methylation Quantification Kit, User Guide, Version 2.0802, 2009

Esteller, Cancer epigenomics: DNA methylomes and histone-modification maps Nature Reviews Genetics: 8, 286-298, 2007

Feinberg and Vogelstein, Hypomethylation distinguishes genes of some human cancers from their normal counterparts. Nature: 301, 89-92, 1983

Grutzmann et al, Sensitive Detection of Colorectal Cancer in Peripheral Blood by Septin 9 DNA Methylation Assay. PLoS ONE 3(11): e3759. doi:10.1371/journal.pone.0003759, 2008

Hervouet et al, Disruption of Dnmt1/PCNA/UHRF1 Interactions Promotes Tumorigenesis from Human and Mice Glial Cells PLoS ONE 5(6): e11333. doi:10.1371/journal.pone.0011333, 2010

Hua et al, Genomic analysis of estrogen cascade reveals histone variant H2A.Z associated with breast cancer progression. Molecular Systems Biology 4; Article number 188; doi:10.1038/msb.2008.25, 2008

Herranz and Esteller, DNA methylation and histone modifications in patients with cancer: potential prognostic and therapeutic targets. Methods Mol Biol. 361:25-62, 2007

Holdenrieder et al, Nucleosomes in serum of patients with benign and malignant diseases. Int. J. Cancer (Pred. Oncol.): 95, 114-120, 2001

*Holdenrieder et al, Nucleosomes in Serum as a Marker for Cell Death. Clin Chem Lab Med; 39(7), 596-605, 2001

Holdenrieder et al, Cell-Free DNA in Serum and Plasma: Comparison of ELISA and Quantitative PCR. Clinical Chemistry: 51(8), 1544-1546, 2005

Holdenreider and Stieber, Clinical use of circulating nucleosomes. Critical Reviews in Clinical Laboratory Sciences; 46(1): 1-24, 2009

Kapoor et al, The histone variant macroH2A suppresses melanoma progression through regulation of CDK8. Nature: 468, 1105-1111, 2010

Mansour et al, The Prognostic Significance of Whole Blood Global and Specific DNA Methylation Levels in Gastric Adenocarcinoma. PLoS ONE 5(12): e15585. doi:10.1371/journal.pone.0015585, 2010

Moore at al, Genomic DNA hypomethylation as a biomarker for bladder cancer susceptibility in the Spanish Bladder Cancer Study: a case—control study. The Lancet Oncology: 9(4), 359-366, 2008

Ogoshi et al, Genome-wide profiling of DNA methylation in human cancer cells. Genomics: In Press, 2011

Pennings et al, DNA methylation, nucleosome formation and positioning. Briefings in functional genomics and proteomics: 3(4), 351-361, 2005

Rodriguez-Paredes and Esteller, Cancer epigenetics reaches mainstream oncology. Nature Medicine: 17(3), 330-339, 2011

Salgame et al, An ELISA for detection of apoptosis. Nucleic Acids Research, 25(3), 680-681, 1997

Sporn et al, Histone macroH2A isoforms predict the risk of lung cancer recurrence. Oncogene: 28(38), 3423-8, 2009

Stroud et al, 5-Hydroxymethylcytosine is associated with enhancers and gene bodies in human embryonic stem cells. Genome Biology: 12:R54, 2011

Tachiwana et al, Structures of human nucleosomes containing major histone H3 variants. Acta Cryst: D67, 578-583, 2011

Ting Hsiung et al, Global DNA Methylation Level in Whole Blood as a Biomarker in Head and Neck Squamous Cell Carcinoma. Cancer Epidemiology, Biomarkers & Prevention: 16(1), 108-114, 2007 van Nieuwenhuijze et al, Time between onset of apoptosis and release of nucleosomes from apoptotic cells: putative implications for sysytemic lupus erythematosus. Ann Rheum Dis; 62: 10-14, 2003

Vasser et al, Measurement of Global DNA Methylation. Genetic Engineering and Biotechnology News: 29(7), 2009

Whittle et al, The Genomic Distribution and Function of Histone Variant HTZ-1 during C. elegans Embryogenesis. PLoS Genet 4(9): 1-17, 2008

Zee et al, Global turnover of histone post-translational modifications and variants in human cells Epigenetics & Chromatin. 3(22): 1-11, 2010

Zhang et al, Analysis of global DNA methylation by hydrophilic interaction ultra high-pressure liquid chromatography tandem mass spectrometry. Analytical Biochemistry: 413(2), 164-170, 2011

The invention claimed is:

1. A method for detecting nucleosomes in a sample which comprises the steps of:
   (i) contacting the sample with three or more binding agents which bind to different or separate nucleosome epitopes;
   (ii) detecting or quantifying the binding of said multiple binding agents to nucleosomes in the sample; and
   (iii) using the presence or degree of such binding as a measure of the presence of nucleosomes in the sample.

2. A method for detecting nucleosomes in a sample which comprises the steps of:
   (i) contacting the sample with a first binding agent which binds to nucleosomes;

(ii) contacting the nucleosomes or sample with two or more second binding agents which bind to different or separate nucleosome epitopes;
(iii) detecting or quantifying the binding of said multiple second binding agents to nucleosomes in the sample; and
(iv) using the presence or degree of such binding as a measure of the presence of nucleosomes in the sample.

3. A method for detecting nucleosomes in a sample which comprises the steps of:
(i) contacting the sample with two or more first binding agents which bind to different or separate nucleosome epitopes;
(ii) contacting the nucleosomes or sample with a second binding agent which binds to nucleosomes;
(iii) detecting or quantifying the binding of said second binding agent to nucleosomes in the sample; and
(iv) using the presence or degree of such binding as a measure of the presence of nucleosomes in the sample.

4. A method for detecting nucleosomes in a sample which comprises the steps of:
(i) contacting the sample with two or more first binding agents which bind to different or separate nucleosome epitopes;
(ii) contacting the nucleosomes or sample with two or more second binding agents which bind to different or separate nucleosome epitopes;
(iii) detecting or quantifying the binding of said second binding agents to nucleosomes in the sample; and
(iv) using the presence or degree of such binding as a measure of the presence of nucleosomes in the sample.

5. A method according to claim 1 wherein the binding agent comprises an antibody.

6. A method according to claim 1 wherein the multiple binding agents for nucleosome epitopes include binders for one or more DNA bases, nucleotides or nucleosides.

7. A method according to claim 1 wherein the multiple binding agents for nucleosome epitopes include binders for one or more histone variants.

8. A method according to claim 1 wherein the multiple binding agents for nucleosome epitopes include binders for one or more post translational histone modifications.

9. A method for detecting nucleosomes in a sample which comprises the steps of:
(i) contacting the sample with two or more anti-nucleosome polyclonal antibodies or purified fractions thereof;
(ii) contacting the nucleosomes or sample with a second antibody or other binder which binds to nucleosomes;
(iii) detecting or quantifying the binding of said second antibody or other binder to nucleosomes in the sample; and
(iv) using the presence or degree of such binding as a measure of the presence of nucleosomes in the sample.

10. A method for detecting nucleosomes in a sample which comprises the steps of:
(i) contacting the sample with a first antibody or other binder which binds to nucleosomes;
(ii) contacting the sample with two or more anti-nucleosome polyclonal second antibodies or purified fractions thereof;
(iii) detecting or quantifying the binding of said second antibody or antibodies to nucleosomes in the sample; and
(iv) using the presence or degree of such binding as a measure of the presence of nucleosomes in the sample.

11. A method according to claim 1 wherein the sample is a biological fluid.

12. A method according to claim 1 wherein the sample is blood, serum or plasma.

13. A method for detecting or diagnosing a disease status in animals or humans which comprises the steps of:
(i) detecting or measuring nucleosomes in a body fluid of a subject according to the methods of claim 1; and
(ii) using the nucleosome level detected to identify the disease status of the subject.

14. A method for assessment of an animal or a human subject for suitability for a medical treatment which comprises the steps of:
(i) detecting or measuring nucleosomes in a body fluid of a subject according to the method of claim 1; and
(ii) using the nucleosome level detected as a parameter for selection of a suitable treatment for the subject.

15. A method for monitoring a treatment of an animal or a human subject which comprises the steps of:
(i) detecting or measuring nucleosomes in a body fluid of a subject according to the method of claim 1;
(ii) repeating the detection or measurement of nucleosomes in a body fluid of a subject on one or more occasions; and
(iii) using any changes in the nucleosome level detected as a parameter for any changes in the condition of the subject.

16. A method according to claim 13 wherein the nucleosome level is detected or measured as one of panel of measurements.

17. A method according claim 13 for use in subjects with actual or suspected cancer, benign tumours, inflammatory disease, autoimmune disease, endometriosis, infectious disease, sepsis, stroke or myocardial infarction.

* * * * *